(12) United States Patent
Reinherz et al.

(10) Patent No.: US 7,247,438 B1
(45) Date of Patent: Jul. 24, 2007

(54) METHODS OF IDENTIFYING AGENTS WHICH ENHANCE CASPASE ACTIVITY

(75) Inventors: Ellis Reinherz, Lincoln, MA (US); Linda Clayton, Jamaica Plain, MA (US); Timothy D. Ocain, Framingham, MA (US); Raymond J. Patch, Framingham, MA (US)

(73) Assignee: Dana-Farber Cancer Institute, Boston, MA (US)

( * ) Notice: Subject to any disclaimer, the term of this patent is extended or adjusted under 35 U.S.C. 154(b) by 0 days.

(21) Appl. No.: 08/948,124

(22) Filed: Oct. 9, 1997

Related U.S. Application Data

(63) Continuation of application No. 08/802,474, filed on Feb. 18, 1997, now abandoned.

(51) Int. Cl.
G01N 33/53 (2006.01)
(52) U.S. Cl. ....................................... 435/7.1
(58) Field of Classification Search ................ 435/7.1, 435/212, 219
See application file for complete search history.

(56) References Cited

U.S. PATENT DOCUMENTS 5,929,042 A 7/1999 Troy et al. ..................... 514/44

FOREIGN PATENT DOCUMENTS

WO WO 97/10711 3/1997

OTHER PUBLICATIONS

AY3 in PTO-1449 Fearnhead et al.*
Gurtu et al Analytical Biochemistry, vol. 251, 98-102, Aug. 15, 1997.*
Robertson, Noreen M., et al., "Baculovirus p35 Inhibits the Glucocorticoid-Mediated Pathway of Cell Death", *Cancer Research*, 57:43-47 (1997).
Bertrand, Richard., et al., "Induction of a Common Pathway of Apoptosis by Staurosporine", *Experimental Cell Research*, 211:314-321 (1994).
Takahashi, A., et al., "CrmA/SPI-2 Inhibition of an Endogenous ICE-related Protease Responsible for Lamin A Cleavage and Apoptotic Nuclear Fragmentation", *The Journal of Biological Chemistry*, 271(51) : 32487-32490 (1996).
Xiang, J., et al., "BAX-Induced Cell Death May Not Require Interleukin 1β-Converting Enzyme-Like Proteases", *Proc. Natl. Acad. Sci.*, 93:14559-14563 (1996).
Takahashi, A., et al., "Inhibition of ICE-Related Proteases (Caspases) and Nuclear Apoptosis by Phenylarsine Oxide", *Experimental Cell Research*, 231:123-131 (1997).
Fowlkes and Pardoll, "Molecular and Cellular Events of T Cell Development", *Adv. Immunol.*, 44:207-264 (1989).
Nossal, "Negative Selection of Lymphocytes", *Cell*, 76:229-239 (1994).

Murphy et al., "Induction by Antigen Of Intrathymic Apoptosis of CD4+CD8+ TCR[10] Thymocytes in Vivo", *Science*, 250:1720-1723 (1990).
Trauth et al., "Monoclonal Antibody-Mediated Tumor Regression by Induction of Apoptosis", *Science*, 245:301-305 (1989).
Yonehara et al., "A Cell-Killing Monoclonal Antibody (ANTI-Fas) to a Cell Surface Antigen Co-Downregulated with the Receptor of Tumor Necrosis Factor", *J. Exp. Med.*, 169:1747-1756 (1989).
Itoh and Nagata, "A Novel Protein Domain Required for Apoptosis", *J. Biol. Chem.*, 268(15) :10932-10937 (1993).
Alderson et al., "Regulation of Apoptosis and T Cell Activation by Fas-Specific mAb", *Intl. Immunol.*, 6(11) :1799-1806 (1994).
Takahashi et al., "Generalized Lymphoproliferative Disease in Mice, Caused by a Point Mutation in the Fas Ligand", *Cell*, 76:969-976 (1994).
Tartaglia et al., "A Novel Domain Within the 55 kd TNF Receptor Signals Cell Death", *Cell*, 74:845-853 (1993).
Chinnaiyan et al., "Signal Transduction by DR3, a Death Domain-Containing Receptor Related to TNFR-1 and CD95", *Science*, 274:990-992 (1996).
Yang and Korsmeyer, "Molecular Thanatopis: A Discourse on the BCL2 Family and Cell Death", *Blood*, 88(2) :386-401 (1996).
Nalin, "Apoptosis Research Enters the ICE Age", *Structure*, 3:143-145 (1995).
Henkart, "ICE Family Proteases: Mediators of All Apoptotic Cell Death?", *Immunity*, 4:195-201 (1996).
Alnemri et al., "Human ICE/CED-3 Protease Nomenclature", *Cell*, 87:171 (1996).
Muzio et al., "FLICE, A Novel FADD-Homologous ICE/CED-3-Like Protease, Is Recruited to the CD95 (Fas/APO-1) Death-Inducing Signaling Complex", *Cell*, 85:817-827 (1996).
Duan et al., "ICE-LAP6, a Novel Member of the ICE/Ced-3 Gene Family, Is Activated by the Cytotoxic T Cell Protease Granzyme B", *J. Biol. Chem.*, 271(28) :16720-16724 (1996).
Fernandes-Alnemri et al., "In vitro Activation of CPP32 and Mch3 by Mch4, a Novel Human Apoptotic Cysteine Protease Containing Two FADD-Like Domains", *Proc. Natl. Acad. Sci. USA*, 93:7464-7469 (1996).
Chinnaiyan et al., "FADD/MORT1 Is a Common Mediator of CD95 (Fas/APO-1) and Tumor Necrosis Factor Receptor-Induced Apoptosis", *J. Biol. Chem.*, 271(9) :4961-4965 (1996).
Duan et al., "ICE-LAP3, a Novel Mammalian Homologue of the *Caenorhabditis elegans* Cell Death Protein Ced-3 Is Activated During Fas- and Tumor Necrosis Factor-Induced Apoptosis", *J. Biol. Chem.*, 271(3):1621-1625 (1996).
Schlegel et al., "CPP32/Apopain Is a Key Interleukin 1β Converting Enzyme-like Protease Involved in Fas-mediated Apoptosis", *J. Biol. Chem.*, 271 (4) :1841-1844 (1996).
Chapman, K.T., "Synthesis of a Potent Reversible Inhibitor of Interleukin-1β Converting Enzyme", *Bioorg. Med. Chem. Lett.*, 2:613-618 (1992).

(Continued)

*Primary Examiner*—Christopher H. Yaen
(74) *Attorney, Agent, or Firm*—Hamilton, Brook, Smith & Reynolds, P.C.

(57) ABSTRACT

Methods for identifying agents which enhance the activity of a caspase according to the invention are described, as well as methods for enhancing caspase activity and methods for enhancing apoptosis in a lymphocyte.

4 Claims, 5 Drawing Sheets

OTHER PUBLICATIONS

Thornberry et al., "A Novel Heterodimeric Cysteine Protease is Required for Interleukin-1β Processing in Monocytes", *Nature*, 356:768-774 (1992).

Thornberry et al., "Inactivation of Interleukin-1β Converting Enzyme by Peptide (Acyloxy) methyl Ketones", *Biochemistry*, 33:3934-3940 (1994).

Rotonda et al., "The Three-Dimensional Structure of Apopain/CPP32, a Key Mediator of Apoptosis", *Nature Struct. Biol.*, 3(7):619-625 (1996).

Pronk et al., "Requirement of an ICE-Like Protease for Induction of Apoptosis and Ceramide Generation by REAPER", *Science*, 271:808-810 (1996).

Fearnhead et al., "An Interleukin-1β- Converting Enzyme-like Protease is a Common Mediator of Apoptosis in Thymocytes", *FEBS Lett.*, 375:283-288 (1995).

Ramarli et al., "Selective Inhibition of Interleukin 2 Gene Function Following Thymocyte Antigen/Major Histocompatibility Complex Receptor Crosslinking: Possible Thymic Selection Mechanism", *Proc. Natl. Acad. Sci. USA*, 84:8598-8602 (1987).

Kappler et al., "T Cell Tolerance by Clonal Elimination in the Thymus", *Cell*, 49:273-280 (1987).

Vasquez et al., "In Vivo and In Vitro Clonal Deletion of Double-Positive Thymocytes", *J. Exp. Med.*, 175:1307-1316 (1992).

Ashton-Rickardt et al., "Evidence for a Differential Avidity Model of T Cell Selection in the Thymus", *Cell*, 76:651-663 (1994).

Hogquist et al., "T Cell Receptor Antagonist Peptides Induce Positive Selection", *Cell*, 76:17-27 (1994).

Sebzda et al. "Positive and Negative Thymocyte Selection Induced by Different Concentrations of a Single Peptide", *Science 263*:1615-1618 (1994).

Williams, "Thyroid Disease: A Case of Cell Suicide?", *Science*, 275:926 (1997).

Walker, et al., "Crystal Structure of the Cystein Protease Interleukin-1β-Converting Enzyme: A $(p20/p10)_2$ Homodimer", *Cell*, 78:343-352 (1994).

Wilson, et al., " Structure and Mechanism of Interleukin-1β Converting Enzyme", *Nature*, 370:270-275 (1994).

Sentman, et al., "bcl-2 Inhibits Multiple Forms of Apoptosis but Not Negative Selection in Thymocytes", *Cell*, 67:879-888 (1991).

Li, et al., "Mice Deficient in IL-1β-Converting Enzyme Are Defective in Productin of Mature IL-1β and Resistant to Endotoxic Shock", *Cell*, 80:401-411 (1995).

Kuida, et al., "Altered Cytokine Export and Apoptosis in Mice Deficient in Interleukin-1β Converting Enzyme", *Science*, 267:2000-2003 (1995).

Rozzo, et al., "Development of the T Cell Receptor Repertoire in *lpr* Mice", *Sem. in Immunol.*, 6:19-26 (1994).

Smith et al., "CrmA Expression in T Lymphocytes of Transgenic Mice Inhibits CD95 (Fas/APO-1)-Transduced Apoptosis, but Does Not Cause Lymphadenopathy or Autoimmune Disease", *EMBO J.*, 15(19):5167-5176 (1996).

Crispe, "Fatal Interactions: Fas-Induced Apoptosis of Mature T Cells", *Immunity*, 1:347-349 (1994).

Clayton, L.K., et al., "T-cell Receptor Ligation by Peptide/MHC Induces Activation of a Caspase in Immature Thymocytes: The Molecular Basis of Negative Selection," *The EMBO Journal*, 16(9): 2282-2293 (1997).

Alam, A., et al., "Specific Activation of the Cysteine Protease CPP32 During the Negative Selection of T Cells in the Thymus," *J. Exp. Med*, 186 (9) : 1503-1512 (1997).

Tewari, M., et al., "Yama/CPP32β, a Mammalian Homolog of CED-3, Is a CrmA-Inhibitable Protease That Cleaves the Death Substrate Poly (ADP-Ribose) Polymerase," *Cell*, 81: 801-809 (1995).

Fernandes-Alnemri, T., et al., "CPP32, a Novel Human Apoptotic Protein with Homology to *Caenorhabditis elegans* Cell Death Protein Ced-3 and Mammalian Interleukin-1β-converting Enzyme," *J. Biol. Chem.*, 268 (49) : 30761-30764 (1994).

\* cited by examiner zVADfmk
(MW = 467)

zVADmk
(MW = 449)

Biotin-DEVDamk
(MW = 848)

Biotin-YVADamk
(MW = 946)

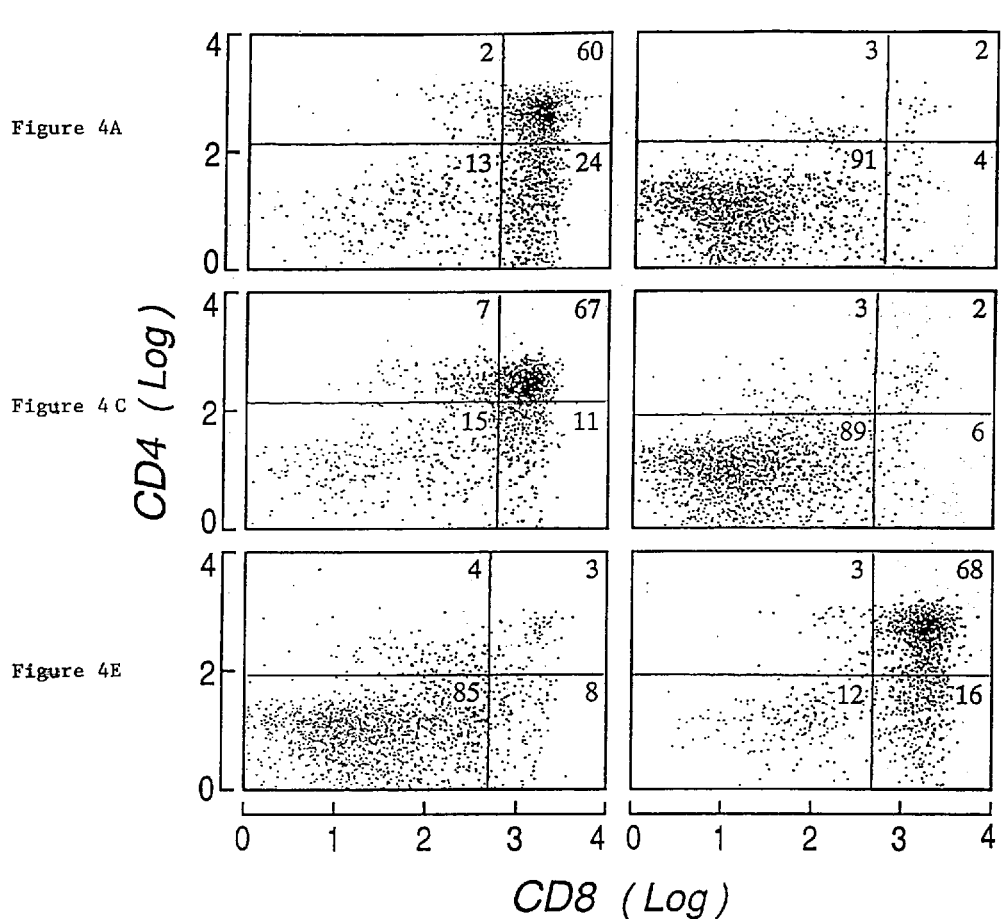

METHODS OF IDENTIFYING AGENTS WHICH ENHANCE CASPASE ACTIVITY

RELATED APPLICATION

This application is a continuation of U.S. application Ser. No. 08/802,474, filed Feb. 18, 1997 (ABN). The teachings of this prior application are incorporated herein by reference in their entirety.

GOVERNMENT FUNDING

Work described herein was supported by an award from the Mathers Foundation and by National Institutes of Health grants AI19807, DK43551 and DK47677 and ES08111. The United States government may have certain rights in the invention.

BACKGROUND OF THE INVENTION

The T cell repertoire is generated through a tightly regulated developmental program of selection or "filtering" in which thymocytes bearing immunologically desirable T cell receptor (TCR) specificities are preserved and those expressing harmful specificities are eliminated (reviewed in Fowlkes and Pardoll, *Adv. Immunol.* 44:207–264 (1989)). T-lineage cells expressing autoreactive TCRs are deleted in the thymus via a process termed negative selection (reviewed in Nossal, *Cell* 76:229–239 (1994)). Multiple lines of evidence utilizing both normal and transgenic mice show that this negative selection process occurs during a restricted stage(s) of thymic differentiation (Fowlkes and Pardoll, *Adv. Immunol.* 44:207–264 (1989); Fowlkes et al., *Nature* 334:620–623 (1988); Kisielow et al., *Nature* 333:742–746 (1988); Murphy et al., *Science* 250:1720–1723 (1990); Vasquez et al., *J. Exp. Med.* 175:1307–1316 (1992); Sebzda et al., *Science* 263:1615–1618 (1994)). The deletion process requires TCR recognition of antigenic peptides displayed on antigen presenting cells in complex with major histocompatibility complex (MHC) class I or class II molecules, and generally involves thymocytes at the double positive (DP) stage of development.

Although the mechanism of negative selection is unknown, the targeted thymocytes die via apoptosis (Murphy et al., *Science* 250:1720–1723 (1990)), a physiologically controlled form of cell death utilized by metazoan organisms during normal development, as well as for homeostasis (reviewed in Steller, *Science* 267:1445–1449 (1995); Vaux, *Proc. Natl. Acad. Sci. USA* 90:86–789 (1993); Vaux and Strasser, *Proc. Natl. Acad. Sci. USA* 93:2239–2244 (1996)). Apoptosis occurs as a consequence of extracellular signalling events such as crosslinking of certain receptors, including CD95 (Trauth et al., *Science* 245:301–305 (1989); Yonehara et al., *J. Exp. Med.* 169:1747–1756 (1988); Itoh and Nagata, *J. Biol. Chem.* 268:10932–10937 (1993); Alderson et al., *Intl. Immunol.* 6:1799–1806 (1994); Takahashi et al., *Cell* 76:969–976 (1994)), TNF receptors (Tartaglia et al., *Cell* 74:845–853 (1993)) and a recently identified Death Receptor 3 (DR3) (Chinnaiyan et al., *Science* 274:990–992 (1996a)) or as a result of growth factor withdrawal (reviewed in Yang and Korsmeyer, *Blood* 88:386–401 (1996)). Upon induction of apoptosis, cells undergo a morphologically characteristic process of nuclear condensation, blebbing of cellular membranes and disintegration into small fragments which are removed by phagocytes (reviewed in Steller, *Science* 267:1445–1449 (1995); Vaux, *Proc. Natl. Acad. Sci. USA* 90:86–789 (1993); Vaux and Strasser, *Proc. Natl. Acad. Sci. USA* 93:2239–2244 (1996)).

SUMMARY OF THE INVENTION

T cell receptors (TCRs) are created by a stochastic gene rearrangement process during thymocyte development, generating thymocytes bearing useful as well as unwanted specificities. Within the latter group, autoreactive thymocytes arise which are subsequently eliminated via a thymocyte-specific apoptotic mechanism, termed negative selection. The molecular basis of this deletion was heretofore unknown.

Work described herein shows that TCR triggering by peptide/MHC ligands activates a caspase in double positive (DP) CD4+CD8+ thymocytes, resulting in their death. Inhibition of this enzymatic activity prevents antigen-induced death of DP thymocytes in fetal thymic organ culture (FTOC) from TCR transgenic mice, as well as apoptosis induced by anti-CD3ε monoclonal antibody and corticosteroids in FTOC of normal C57BL/6 mice. Hence, a common enzyme mediates immature thymocyte susceptibility to cell death.

Accordingly, this invention pertains to an isolated caspase or procaspase expressed in immature thymocytes, or an active derivative or fragment thereof, wherein said caspase is necessary for apoptosis. The caspase is characterized by its ability to be triggered by TCR stimulation with peptide/MHC, anti-CD3ε or other anti-TCR-specific monoclonal antibody, or corticosteroids in thymocytes. In one embodiment, the caspase is a fragment having caspase activity, e.g., binding or enzymatic activity. In another embodiment, the caspase or procaspase is a derivative possessing substantial sequence identity with the endogenous caspase or procaspase. In particular embodiments, the caspase or procaspase is purified to homogeneity or is substantially free of other thymocyte proteins.

The invention also pertains to an isolated nucleic acid molecule which encodes a caspase or procaspase expressed immature thymocytes and necessary for apoptosis, or an active derivative or fragment thereof. In one embodiment, the encoded caspase is a fragment having caspase activity. In another embodiment, the encoded caspase or procaspase is a derivative possessing substantial sequence identity with the endogenous caspase or procaspase. In particular embodiments, the isolated nucleic acid molecule encodes a caspase or procaspase with the same amino acid sequence as the endogenous caspase or procaspase. In another embodiment, the isolated nucleic acid molecule has the same nucleotide sequence as the endogenous gene encoding the caspase or procaspase.

The invention also relates to DNA constructs comprising the nucleic acid molecules described above operatively linked to a regulatory sequence, and to recombinant host cells, such as bacterial cells, fungal cells, plant cells, insect cells and mammalian cells, comprising the nucleic acid molecules described above operatively linked to a regulatory sequence. The invention also pertains to an antibody, or an antigen-binding fragment thereof, which selectively binds to the caspase or procaspase, or an active derivative or fragment thereof; in a particular embodiment, the antibody is a monoclonal antibody. The invention also relates to a method for assaying the presence of a caspase or procaspase, present in immature thymocytes and necessary for apoptosis, in a cell, e.g., in a tissue sample, comprising contacting said cell with an antibody which specifically binds to the caspase or procaspase.

The invention further relates to methods of inhibiting apoptosis in a lymphocyte population, particularly in immature thymocytes, comprising contacting the lymphocyte population with an agent which inhibits the activity of the caspase, such as in administering to a subject an agent which inhibits the activity of the caspase. For example, the invention also pertains to methods of enhancing an immune response against an antigen in a subject by administering to the subject an effective amount of an agent which inhibits the activity of the caspase along with the selected antigen. In a particular embodiment, the antigen is a cancer antigen.

The present invention also relates to an assay for identifying agents which alter the activity of the caspase implicated in lymphocyte, particularly thymocyte, apoptosis. For example, the caspase, or an active fragment or derivative thereof, can be contacted with a caspase substrate in the presence of an agent to be tested, and the level of lymphocyte apoptosis can be assessed.

By inhibiting apoptosis as described above, the down regulation and/or deletion of lymphocytes, particularly thymocytes, can be prevented or inhibited; thus, DP thymocytes are prevented from self-destruction. This results in a T cell receptor population with an increased proportion of autoreactive T cells; that is, there is an increased occurrence of T cells which have specificity for the host animal's own cells. This is particularly advantageous when it is desirable to generate an immune response against the host's own cells (an autoimmune response), such as, for example, in the case of tumor growth and cancers such as leukemia and melanomas. This technology is especially useful for preparing animal models having depleted T cell populations and animal models for autoimmune disease.

BRIEF DESCRIPTION OF THE DRAWINGS

FIG. 2A shows the results when thymic extracts, prepared from PBS, VSV8 or SEV9 injected N15 tg RAG-2$^{-/-}$ H-2$^b$ mice, were incubated 15 minutes with (+) or without (−) 2 mM biotin-DEVDamk. Each lane contained thymic extract equivalent to 2 million thymocytes. VSV8 peptide injections were performed 1.5 hours prior to harvest. FIG. 2B shows the results when 140 ng of purified, recombinant Mch2a and 3.5 ng of purified, recombinant Yama were incubated for 15 minutes with 2 mM biotin-DEVDamk. FIG. 2C shows the results when thymic extracts, prepared from mice 2 hours after VSV8 peptide injection, were incubated 15 minutes with 2 mM biotin-DEVDamk alone, 2 mM zVADfmk alone, or preincubated 15 minutes with an excess of 1000×, 500×, 100×, 10× or an equal concentration of zVADfmk. FIG. 2D shows the results when thymic extracts, isolated from mice 2 hours after VSV8 peptide injection, were incubated for 15 minutes with 2 mM biotin-DEVDamk alone (−), or, alternatively, incubated for 15 minutes with 200 mM zVADfmk or zVADmk and then biotin-DEVDamk added to 2 mM for another 15 minutes.

FIGS. 4A–4F illustrate that a caspase inhibitor blocks peptide/MHC-induced deletion of DP thymocytes. FACS analysis of FTOC from N15 TCRtg RAG-2$^{-/-}$H-2$^b$ mice following 18 hour treatment with no addition (4A); addition of 10 μM VSV8 peptide (4B); 2 hours with 100 μM zVADfmk followed by 18 hours with 10 μM VSV8 (4C); 2 hours with 100 μM zVADmk followed by 18 hours with 10 μM VSV8 (4D); 2 hours with 0.25% DMSO followed by 18 hours with 10 μM VSV8 (4E); and 18 hours with 10 μM SEV9 (4F). The numbers within the quadrants represent the percent of cells in that quadrant.

DETAILED DESCRIPTION OF THE INVENTION

Figure 1:
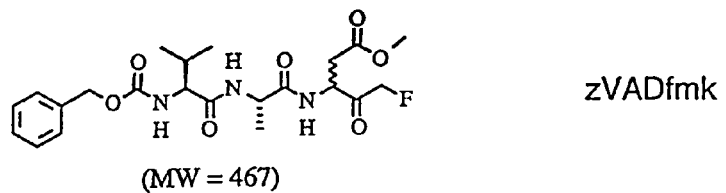
FIG. 1 illustrates structures of the peptide-based caspase inhibitors and related compounds. The structures of the peptide-based inhibitor analogues used in these studies are shown along with their molecular weight as verified by mass spectrometry. The common names of the compounds are also given.
Figure 1:
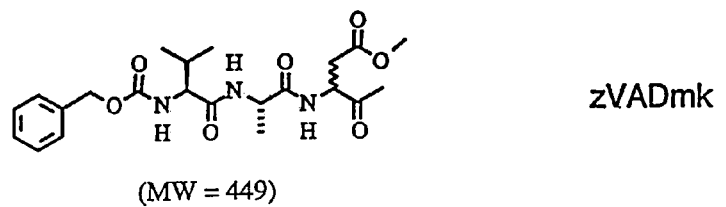
Figure 1:
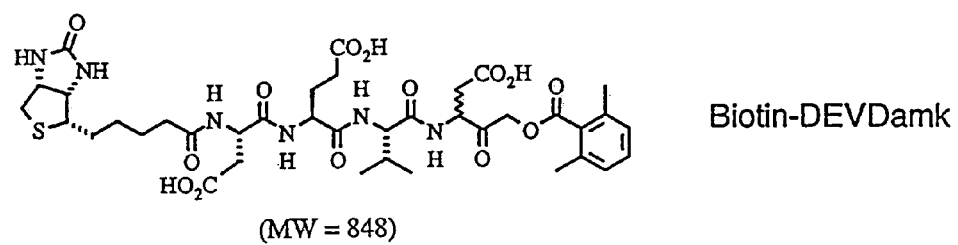
Figure 1:
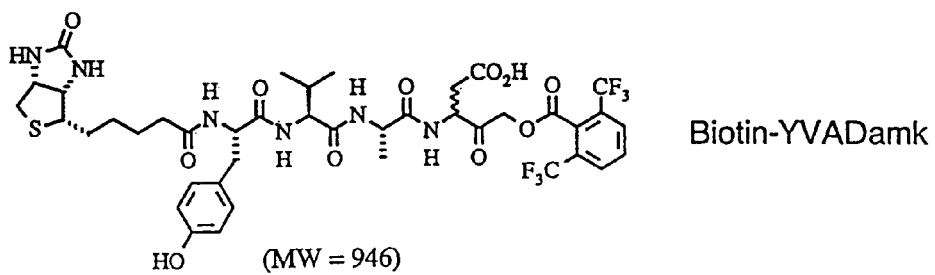

The T cell repertoire is generated through a tightly regulated developmental program of selection or "filtering", in which thymocytes bearing immunologically desirable TCR specificities are preserved and those expressing harmful specificities are eliminated (reviewed in Fowlkes and Pardoll (1989)). T-lineage cells expressing autoreactive TCRs are deleted in the thymus via a process termed negative selection (reviewed in Nossal (1994)). Although the mechanism of negative selection is unknown, the targeted thymocytes die via apoptosis (Murphy et al. (1990)), a physiologically controlled form of cell death utilized by metazoan organisms during normal development as well as for homeostasis (reviewed in Steller (1995); Vaux (1993); Vaux & Strasser (1996)).

Recent analyses of the death pathways in various systems have begun to delineate the biochemical basis of apoptosis. Particularly, activation of interleukin 1 converting enzyme-like (ICE-like) cysteine proteases (now termed caspases) has proven to be a hallmark of apoptotic death (reviewed in Nalin, *Structure* 3:143–145 (1995); Henkart, *Immunity* 4:195–201 (1996)). There are presently ten human homologues of the ced 3 cysteine protease first defined by genetic analysis of cell death in *Caenorhabditis elegans* (Alnemri et al., *Cell* 87:171 (1996); Muzio et al., *Cell* 85:817–827 (1996); Duan et al., *J. Biol. Chem.* 271:16720–16724 (1996a); Fernandes-Alnemri et al., *Proc. Natl. Acad. Sci. USA* 93:7464–7469 (1996)). These enzymes exist as inactive proenzymes which become active when cleaved to subunits of ~17–20 kd and ~10–12 kd.

The molecular structures of ICE (caspase-1) and Yama (caspase-3) have been determined (Walker et al., *Cell* 78:343–352 (1994); Wilson et al., *Nature* 370:270–275 (1994); Rotonda et al., *Nature Struct. Biol.* 3:619–625 (1996)). The active enzymes exist as tetramers made up of two large and two small subunits. Comparison of these structures suggests that the caspase family falls into two major groups: those that most resemble caspase-1, and those that most resemble caspase-3 (and also ced-3). The substrate binding pockets of these two groups have distinct differences pointing to potentially unique substrate specificities.

The active sites contain a critical cysteine within the canonical pentapeptide, QACR/QG (SEQ ID NO: 1), and R and Q residues (Arg 179, Gln 283 and Arg 341, for example, in caspase 3) conserved among all caspase family members. A unique characteristic of these enzymes is that they cleave after an aspartic acid residue in their substrate (Sleath et al., *J. Biol. Chem.* 265:14526–14528 (1990); Howard et al., *J. Immunol.* 147:2964–2969 (1991); Thornberry et al., *Biochemistry* 33:3934–3940 (1994)). Thus, the fact that activation of these enzymes occurs by cleavage at aspartic acid residues suggests both autocatalytic capabilities and the possibility of a cascade of various cysteine proteases, with one family member activating others during apoptosis.

To date, the characterization of caspase enzymatic activities has typically been investigated using transfected cell lines. Hence, the physiological roles of most of these cysteine proteases in vivo are unclear. Two cysteine proteases, caspase-3 and ICE-LAP3 (caspase-7), have been shown to be proteolytically activated by apoptotic stimuli, implying a central role for this family of enzymes in cell death in vivo (Chinnaiyan et al., *J. Biol. Chem.* 271:4961–4965 (1996b); Duan et al., *J. Biol. Chem.* 271:1621–1625 (1996b); Schlegel et al., *J. Biol. Chem.* 271:1841–1844 (1996)).

Given the link between apoptosis and negative selection in the thymus, work described herein examines the potential role of caspase activity in antigen-triggered deletion of CD4+CD8+ double positive (DP) fetal and adult thymocytes. Using peptide-based enzyme substrates, it is shown herein that TCR ligation by peptide/MHC activates a procaspase in DP thymocytes, which then causes cell death; specific enzyme inhibitors block this death process. These findings provide the molecular basis for negative selection.

Caspases are irreversibly inhibited by tri- or tetrapeptide sequences (VAD, YVAD (SEQ ID NO: 2) and/or DEVD (SEQ ID NO: 3)) linked to a chemical moiety such as fluoromethylketone (fmk) or various acyloxymethylketones (amk) which covalently modify the enzyme, thereby inactivating its catalytic function (Chapman, K. T., *Bioorg. Med. Chem. Lett.* 2:613–618 (1992); Thornberry et al., et al., *Nature* 356:768–774 (1992); Thornberry et al., *Biochemistry* 33:3934–3940 (1994); Rotonda et al., *Nature Struct. Biol.* 3:619–625 (1996)). The peptide-based inhibitor, N-benzyloxycarbonyl-Val-Ala-Asp(OMe)-fluoromethylketone (zVADfmk), blocks the induction of apoptosis induced by expression of REAPER protein when added to *Drosophila* Schneider cells (Pronk et al., *Science* 271:808–810 (1996)); such experiments demonstrate that REAPER-induced apoptosis requires activation of a caspase.

In order to analyze the effect of inhibition of members of the caspase family of cysteine proteases on negative selection in the thymus, a fetal thymocyte organ culture (FTOC) system was utilized in the work described herein. FTOC was chosen over both in vivo whole animal studies or in vitro cell suspension cultures for several reasons. First, FTOC allows analysis of the effects of pharmaceutical agents on thymocyte development in a system which more closely mimics in vivo conditions than does thymocyte suspension culture. Second, pharmacophores which cannot be utilized in whole mice, either due to systemic toxicity or limitations in their bioavailability, can be assayed easily in FTOC. Furthermore, the relatively small volumes required minimize the amount of necessary chemical.

As work described herein demonstrates, peptide/MHC-induced negative selection of DP thymocytes involves the activation of a thymic caspase. Double staining with anti-CD4 mAb and N-(biotinylaspartylglutamylvalinyl)aspartic acid [(2,6-dimethylbenzoyl)oxy]methyl ketone (biotin-DEVDamk) (a biotinylated substrate of cysteine proteases) of thymic sections from both fetal and adult N15 TCRtg RAG-$2^{-/-}$ H-$2^b$ mice demonstrates that the caspase is activated in the DP thymocyte subpopulation within a time frame of $\leq 2$ hours. Subsequently, at 4 hours, a tremendous increase in the number of apoptotic thymocytes was observed, as determined by TUNEL assays of histological sections of thymuses. At 18 hours, by FACS analysis and immunohistological analysis, >90% of the DP thymocyte population is deleted. Both the disappearance of DP thymocytes and the increase in numbers of apoptotic cells in histological sections are blocked by treatment of FTOC with zVADfmk, a peptide-based inhibitor of cysteine proteases.

Biochemical analysis of thymic lysates prepared from adult N15 TCRtg RAG-$2^{-/-}$ H-$2^b$ mice using biotin-DEVDamk confirms the induction of an active caspase within 2 hours after tail vein injection of VSV8 antigen (RGYVYQGL) (SEQ ID NO: 9). This enzyme activation is specifically induced, as it is not activated in control (PBS) or animals treated with the irrelevant Sendai virus-derived peptide (FAPGNYPAL; SEQ ID NO: 4) (SEV9). Pretreatment of the thymic lysates with an excess of the irreversible inhibitor zVADfmk prevents binding of the biotin-DEVDamk to the caspase, while the chemically-related control compound zVADmk, a compound identical to zVADfmk (FIG. 1) except for the absence of the fluoride atom which is required for the irreversible inhibition of caspases, does not. zVADmk also has no effect on antigen-induced depletion of DP thymocytes in FTOC or the appearance of TUNEL positive cells in histological sections upon VSV8 peptide treatment of FTOC. Thus, the zVADfmk which blocks depletion of DP thymocytes in FTOC also blocks binding of the biotin-DEVDamk to its substrate. These results support the conclusion that the caspase functionally inhibited by zVADfmk in FTOC is the same as that detected by biotin-DEVDamk by Western blot analysis. Activation of this caspase is the molecular basis for negative selection of DP thymocytes.

Figure 3:
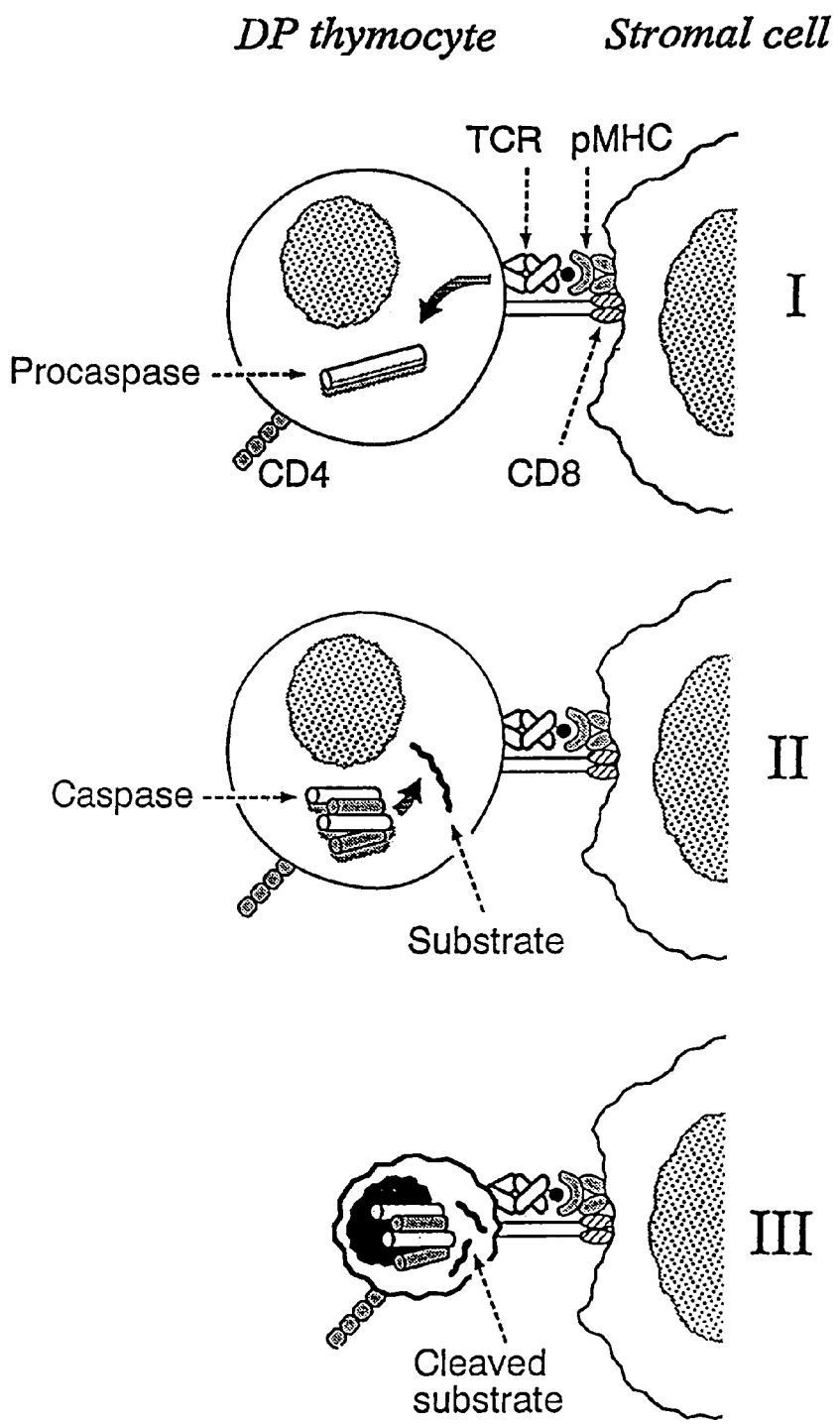
FIG. 3 illustrates a model of TCR regulated activation of thymic caspase, particularly a schematic model of the process by which peptide/MHC (pMHC) on an antigen presenting cell (stromal cell) triggers the TCR of an immature DP thymocyte, resulting in the activation of a caspase, cleavage of thymocyte protein substrates and thymocyte apoptosis. Note that selective engagement of the CD8 co-receptor with the TCR and pMHC is shown, consistent with a class I restricted TCR such as N15; in the case of a class II restricted TCR, CD4 rather than CD8 would be engaged. The large arrow indicates that TCR mediated signal transduction results in cleavage of procaspase to the active caspase tetramer. The tetramer then cleaves certain cellular substrates, resulting in negative selection.

The above data can be schematically represented as shown in FIG. 3. The TCR of the double positive thymocyte binds the peptide/MHC (pMHC) on an antigen presenting stromal cell with the restricted association of the CD4 or CD8 co-receptor; in the case of the N15 TCR transgenic mouse, the CD8 co-receptor is involved. If the affinity of the TCR/peptide/MHC interaction is of sufficient magnitude, as is true for the N15 TCR and VSV8/$K^b$ complex (pMHC), the thymocyte is triggered to undergo negative selection. Upon this triggering, a procaspase is cleaved to form an active tetramer which catabolizes cellular substrates, resulting in apoptosis of the DP thymocyte. It is reasonable that a similar mechanism is operative via B cell receptors in early B cell development, and, thus, the methods described herein are applicable to both B lymphocytes and T lymphocytes (Nossal, *Cell* 76:229–239 (1994)).

Analysis of the Western blots demonstrates that there is likely only one enzyme activated, since there is a single predominant band by gel analysis. A less intense band migrating slightly faster than the major band may be a degradation product or post-translational modification. However, the possibility that a second caspase might be activated cannot be excluded. If the latter is the case, then both enzymes are blocked by the zVADfmk inhibitor.

Studies to date defining substrates and inhibitors of known caspases offer additional insights into the possible identity of the thymic caspase. Peptide-based inhibitors serve to characterize different substrate specificities among the caspase family members. The tetrapeptide aldehyde Ac-YVAD-CHO inhibits caspase-1 at ~10,000-fold lower concentration than that required to inhibit caspase-3. In contrast, Ac-DEVD-CHO inhibits caspase-3 49 times better than caspase-1 (Rotonda et al., *Nature Struct. Biol.* 3:619–625 (1996)).

Utilizing thymic lysates from VSV8-injected N15 TCRtg RAG$^{-/-}$ H-2$^b$ mice, biotin-YVADamk failed to detect the caspase readily revealed by biotin-DEVDamk. The recombinant caspase-3 protein used as a positive control was detected by biotin-YVADamk only when 100 times more of the enzyme was used. The crystal co-complex structures of caspase-1 and caspase-3 and their inhibitors clarify the observed substrate specificities (Walker et al., *Cell* 78:343–352 (1994); Wilson et al., *Nature* 370:270–275 (1994); Rotonda et al., *Nature Struct. Biol.* 3:619–625 (1996)): the S4 subsite in caspase-1 is a hydrophobic depression into which a tyrosine residue fits nicely as in the ac-YVAD-CHO peptide aldehyde inhibitor. In contrast, the comparable S4 subsite in caspase-3 forms a narrow pocket fitting tightly around an aspartic acid residue as in the ac-DEVD-CHO peptide aldehyde inhibitor. This substrate difference suggests that the thymic caspase should be grouped with the caspase-3-like cysteine proteases rather than the caspase-1-like.

Studies with proteins which inhibit functional enzymatic activity further serve to categorize the caspase family members. Bcl-2, first identified as a proto-oncogene in B-cell follicular lymphomas, inhibits some forms of apoptotic cell death including death induced by ICH-1 (caspase-2) (reviewed in Yang and Korsmeyer, *Blood* 88:386–401 (1996)). The cytokine response modifier, crmA, derived from the cowpox virus, inhibits caspase-1 but not caspase-2. At high concentrations, however, crmA also inhibits caspase-3 (Nicholson et al., *Nature* 376:37–43 (1995); Tewari et al., *Cell* 81:801–809 (1995)). Negative selection is unaffected in Bcl-2 (Sentman et al., *Cell* 67:879–888 (1991)) and caspase-1 (L1 et al., *Cell* 80:401–411 (1995); Kuida et al., *Science* 267:2000–2003 (1995)) knockout animals. The crmA transgenic mouse in which crmA is directed to the T-cell compartment via a CD2 enhancer demonstrates a phenotype in which CD95-induced peripheral T cell apoptosis is inhibited, but negative selection in the thymus appears to be unaffected (Smith et al., *EMBO J.* 15:5167–5176 (1996)). The inhibitors Bcl-2 and crmA have complementary effects in that the crmA transgene does not affect γ-irradiation or dexamethasone-induced apoptosis, while Bcl-2 inhibits both. Neither Bcl-2 nor crmA transgenes, however, affect negative selection. One would expect that the thymic caspase described here would not be inhibited by crmA or by Bcl-2.

Analysis of apoptotic pathways triggered by different stimuli in cells transfected with Bcl-2 and crmA have been used to suggest molecular ordering of particular caspases within death pathways, and further imply the presence of a cascade of caspases with one member activating others. Studies suggest a molecular ordering in which Bcl-2 and Bcl-x$_L$, a homologue of Bcl-2, function upstream of caspase-3 and caspase-7 (Chinnaiyan et al., *J. Biol. Chem.* 271:4373–4576 (1996c); crmA also appears to function by inhibiting a protease upstream of caspase-3 and caspase-7, but in a different pathway from that inhibited by Bcl-2 (Chinnaiyan et al., *J. Biol. Chem.* 271:4373–4576 (1996c)).

Granzyme B is a serine protease which cleaves at an aspartic acid in its substrate (Caputo et al., *Nature Struc. Biol.* 1:364–367 (1994)) and is activated only in cytolytic T lymphocytes (Hanson and Ley, *Mol. Cell. Biol.* 10:5655–5662 (1990); Hanson et al., *J. Biol. Chem.* 266: 24433–24438 (1991); Heusel et al., *J. Biol. Chem.* 266: 6152–6158 (1991)). Post-activation, granzyme B is transferred into target cells, where it initiates caspase cleavage, notably of caspase-3 (Darmon et al., *Nature* 377:446–448 (1995); Quan et al., *Proc. Natl. Acad. Sci. USA* 93:1972–1976 (1996)). Thus, proteases other than caspases may activate these enzymes, initiating the cascade of caspase functional programs leading to cell death. ICH-3 has also been shown to be activated by granzyme B (Wang et al., *J. Biol. Chem.* 271:20580–20587 (1996)). Ordering of ICH-3 activity places it upstream of caspase-1 in the granzyme B pathway, and upstream of caspase-3 as well.

Certain cysteine proteases have been analyzed by targeted gene disruption. Caspase-1 knockout animals do not have a generalized death defect, suggesting that this enzyme may not be central to all death pathways (Li et al., *Cell* 80:401–411 (1995); Kuida et al., *Science* 267:2000–2003 (1995)). The CD95-induced death pathway is affected in these animals, but negative selection is not altered in mlr mice bearing the spontaneous CD95 mutation (reviewed by Rozzo et al., *Sem. in Immunol.* 6:19–26 (1994)). ICH-1 and ICH-3 mouse cysteine proteases have also been knocked out; mAb induced-depletion of DP thymocytes appears to proceed normally in these animals, suggesting that neither of these proteases is the caspase important in thymic selection.

Furthermore, cleavage of poly(ADP-ribose) polymerase (PARP) in thymic lysates of C57BL/6 animals injected intraperitoneally with anti-CD3ε mAb was not observed (data not shown). Since PARP is a substrate of caspase-3, this suggests that caspase-3 is also not responsible for the observed thymic apoptosis. Assuming that the crmA levels were sufficiently high in the crmA transgenic mice described above (Smith et al., *EMBO J.* 15:5167–5176 (1996)), then caspase-3 would have been inhibited in those mice, and yet negative selection was unaffected. The absence of an effect on thymopoiesis in caspase-3 knockout mice is also consistent with this notion. These studies suggest that the thymic caspase is not caspase-1, caspase-3, ICH-1 or ICH-3.

Western blots demonstrate that there is likely only one enzyme activated, since there is a single predominant band by gel analysis. A less intense band migrating slightly faster than the major band may be a degradation product or post-translational modification. Either or both of these bands can be isolated and purified by HPLC, and the resulting purified protein can be sequenced. Alternatively, the purified protein can be enzymatically digested by methods known in the art to produce peptide fragments which can be sequenced. The sequencing can be performed, for example, by the methods of Wilm et al. (*Nature* 379(6564):466–469 (1996)). Degenerate oligonucleotide primers can be synthesized based on the amino acid sequence of the purified protein or fragments of the purified protein, and the corresponding DNA fragment can be amplified by polymerase chain reaction (PCR), as described in, e.g., *Current Protocols in Molecular Biology*, John Wiley & Sons, N.Y. (1989). The amplified DNA can be radiolabelled and used as a probe for screening a cDNA library derived from N15 thymocyte mRNA in λzap express or other suitable vector. Corresponding clones can be isolated, DNA can obtained following in vivo excision, and the cloned insert can be sequenced in either or both orientations, such as by the methods described in *Current Protocols in Molecular Biology*, John Wiley & Sons, N.Y. (1989), to identify the correct reading frame encoding a protein of the appropriate molecular weight. Using these or similar methods, the caspase protein(s) and the DNA encoding the protein can be isolated, sequenced and further characterized.

Accordingly, the invention pertains to an isolated nucleotide sequence encoding the caspase enzyme. As appropriate, nucleic acid molecules of the present invention can be RNA, for example, mRNA, or DNA, such as cDNA and genomic DNA. DNA molecules can be double-stranded or single-stranded; single stranded RNA or DNA can be either the coding, or sense, strand or the non-coding, or antisense, strand. Preferably, the nucleic acid molecule comprises at least about 25 nucleotides, more preferably at least about 50 nucleotides, and even more preferably at least about 200 nucleotides. The nucleotide sequence can be only that which encodes at least a fragment of the amino acid sequence of the caspase protein; alternatively, the nucleotide sequence can include at least a fragment of the caspase amino acid coding sequence along with additional non-coding sequences such as introns and non-coding 3' and 5' sequences (including regulatory sequences, for example). Additionally, the nucleotide sequence can be fused to a marker sequence, for example, a sequence which encodes a polypeptide to assist in isolation or purification of the polypeptide. Such sequences include, but are not limited to, those which encode a glutathione-5-transferase (GST) fusion protein and those which encode a hemaglutin A (HA) peptide marker from influenza.

As used herein, an "isolated" gene or nucleotide sequence is intended to mean a gene or nucleotide sequence which is not flanked by nucleotide sequences which normally (in nature) flank the gene or nucleotide sequence (as in genomic sequences) and/or has been completely or partially purified from other transcribed sequences (as in a cDNA or RNA library). Thus, an isolated gene or nucleotide sequence can include a gene or nucleotide sequence which is synthesized chemically or by recombinant means. Thus, recombinant DNA contained in a vector are included in the definition of "isolated" as used herein. Also, isolated nucleotide sequences include recombinant DNA molecules in heterologous host cells, as well as partially or substantially purified DNA molecules in solution. In vivo and in vitro RNA transcripts of the DNA molecules of the present invention are also encompassed by "isolated" nucleotide sequences. Such isolated nucleotide sequences are useful in the manufacture of the encoded protein, as probes for isolating homologous sequences (e.g., from other mammalian species), for gene mapping (e.g., by in situ hybridization with chromosomes), or for detecting expression of the caspase gene in tissue (e.g., human tissue), such as by Northern blot analysis.

The present invention also pertains to nucleotide sequences which are not necessarily found in nature but which do, in fact, encode the caspase. Thus, DNA molecules which comprise a sequence which is different from the naturally-occurring nucleotide sequence but which, due to the degeneracy of the genetic code, encode the caspase of the present invention are the subject of this invention. The invention also encompasses variations of the nucleotide sequences of the invention, such as those encoding portions, analogues or derivatives of the caspase protein. Such variations can be naturally-occurring, such as in the case of allelic variation, or non-naturally-occurring, such as those induced by various mutagens and mutagenic processes. Included variations include, but are not limited to, addition, deletion and substitution of one or more nucleotides which can result in conservative or non-conservative amino acid changes, including additions and deletions. Preferably, the nucleotide or amino acid variations are silent; that is, they do not alter the characteristics or activity of the caspase enzyme.

The invention described herein also relates to fragments of the isolated nucleic acid molecules described above. The term "fragment" is intended to encompass a portion of a nucleotide sequence described herein which is from at least about 25 contiguous nucleotides to at least about 50 contiguous nucleotides or longer in length; such fragments are useful as probes, e.g., for diagnostic methods and also as primers. Particularly preferred primers and probes selectively hybridize to the nucleic acid molecule encoding the caspase described herein. For example, fragments which encode antigenic regions of the caspase protein described herein are useful.

The invention also pertains to nucleotide sequences which hybridize under low, medium or high stringency hybridization conditions (e.g., for selective hybridization) to a portion of a nucleotide sequence described herein. Appropriate stringency conditions are known to those skilled in the art or can be found in standard texts such as *Current Protocols in Molecular Biology*, John Wiley & Sons, N.Y. (1989), 6.3.1–6.3.6. Such hybridizable nucleotide sequences are useful as probes and primers for diagnostic applications.

Accordingly, the invention pertains to nucleotide sequences which have a substantial identity with the nucleotide sequences described herein; particularly preferred are nucleotide sequences which have at least about 90%, and more preferably at least about 95% identity with nucleotide sequences described herein. Particularly preferred in this instance are nucleotide sequences encoding polypeptides having at least one activity of the novel caspase described herein. For example, preferred nucleotide sequences encoding a polypeptide having the same or similar biological activity as the novel caspase and nucleotide sequences encoding a polypeptide with the same or similar immunogenic or antigenic properties as the novel caspase are within the scope of the invention. As used herein, activities of the caspase include, but are not limited to, catalytic activity, binding function, antigenic function and oligomerization function.

This invention also pertains to an isolated protein or polypeptide which is a novel caspase enzyme present in immature thymocytes and necessary for apoptosis. The caspase is characterized by its ability to be triggered by TCR stimulation with peptide/MHC, anti-CD3ε or other anti-TCR-specific monoclonal antibody, or corticosteroids in thymocytes. The caspase of the invention can be partially or substantially purified (e.g., purified to homogeneity), and/or is substantially free of other thymocyte proteins. According to the invention, the amino acid sequence of the polypeptide can be that of the naturally-occurring protein or can comprise alterations therein. Such alterations include conservative or non-conservative amino acid substitutions, additions and deletions of one or more amino acids; however, such alterations should preserve at least one activity of the caspase, i.e., the altered or mutant protein should be an active derivative of the naturally-occurring protein. For example, the mutation(s) can preferably preserve the three dimensional configuration of the binding and/or catalytic site of the native protein. The presence or absence of caspase activity or activities can be determined by various functional assays as described herein. Moreover, amino acids which are essential for the function of the caspase can be identified by methods known in the art. Particularly useful methods include identification of conserved amino acids in the family or subfamily of caspases, site-directed mutagenesis and alanine-scanning mutagenesis (for example, Cunningham and Wells, *Science* 244:1081–1085 (1989)), crystallization and nuclear magnetic resonance. The altered polypeptides produced by these methods can be tested for particular biologic activities, including immunogenicity and antigenicity.

Specifically, appropriate amino acid alterations can be made on the basis of several criteria, including hydrophobicity, basic or acidic character, charge, polarity, size, the presence or absence of a functional group (e.g., —SH or a glycosylation site), and aromatic character. Assignment of various amino acids to similar groups based on the properties above will be readily apparent to the skilled artisan; further appropriate amino acid changes can also be found in Bowie et al. (*Science* 247:1306–1310(1990)).

The caspase polypeptide can also be a fusion protein comprising all or a portion of the caspase amino acid sequence fused to an additional component. Additional components, such as radioisotopes and antigenic tags, can be selected to assist in the isolation or purification of the polypeptide or to extend the half life of the polypeptide; for example, a hexahistidine tag would permit ready purification by nickel chromatography. Furthermore, polypeptides of the present invention can be procaspases; procaspases are molecules which are cleaved to form an active tetramer (the caspase).

Also included in the invention are polypeptides which are at least about 40% identical to the novel caspase described herein. However, polypeptides exhibiting lower levels of identity are also useful, particular if they exhibit high, e.g., at least about 40%, identity over one or more particular domains of the protein. For example, polypeptides sharing high degrees of identity over domains necessary for particular activities, including binding and enzymatic activity, are included herein.

Polypeptides described herein can be isolated from naturally-occurring sources, chemically synthesized or recombinantly produced. Polypeptides or proteins of the present invention can be used as a molecular weight marker on SDS-PAGE gels or on molecular sieve gel filtration columns using art-recognized methods.

The invention also provides expression vectors containing a nucleic acid sequence encoding a polypeptide which is a caspase present in immature thymocytes and necessary for apoptosis, operably linked to at least one regulatory sequence. Many such vectors are commercially available, and other suitable vectors can be readily prepared by the skilled artisan. "Operably linked" is intended to meant that the nucleotide sequence is linked to a regulatory sequence in a manner which allows expression of the nucleic acid sequence. Regulatory sequences are art-recognized and are selected to produce a polypeptide which is a caspase. Accordingly, the term "regulatory sequence" includes promoters, enhancers, and other expression control elements which are described in Goeddel, *Gene Expression Technology: Methods in Enzymology* 185, Academic Press, San Diego, Calif. (1990). For example, the native regulatory sequences or regulatory sequences native to the transformed host cell can be employed. It should be understood that the design of the expression vector may depend on such factors as the choice of the host cell to be transformed and/or the type of protein desired to be expressed. For instance, the polypeptides of the present invention can be produced by ligating the cloned gene, or a portion thereof, into a vector suitable for expression in either prokaryotic cells, eukaryotic cells or both (see, for example, Broach, et al., *Experimental Manipulation of Gene Expression*, ed. M. Inouye (Academic Press, 1983) p. 83; *Molecular Cloning: A Laboratory Manual*, 2nd Ed., ed. Sambrook et al. (Cold Spring Harbor Laboratory Press, 1989) Chapters 16 and 17). Typically, expression constructs will contain one or more selectable markers, including, but not limited to, the gene that encodes dihydrofolate reductase and the genes that confer resistance to neomycin, tetracycline, ampicillin, chloramphenicol, kanamycin and streptomycin resistance.

Prokaryotic and eukaryotic host cells transfected by the described vectors are also provided by this invention. For instance, cells which can be transfected with the vectors of the present invention include, but are not limited to, bacterial cells such as *E. coli* (e.g., *E. coli* K12 strains, *Streptomyces, Pseudomonas, Serratia marcescens* and *Salmonella typhimurium*, insect cells (baculovirus), including *Drosophila*, fungal cells, such as yeast cells, plant cells and mammalian cells, such as thymocytes, Chinese hamster ovary cells (CHO), and COS cells.

Thus, a nucleotide sequence derived from the cloning of the caspase described herein can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect, plant or mammalian) or prokaryotic (bacterial cells), are standard procedures used in producing other well known proteins. Similar procedures, or modifications thereof, can be employed to prepare recombinant proteins according to the present invention by microbial means or tissue-culture technology. Accordingly, the invention pertains to the production of caspase proteins or polypeptides by recombinant technology.

The proteins and polypeptides of the present invention can be isolated or purified (e.g., to homogeneity) from recombinant cell culture by a variety of processes. These include, but are not limited to, anion or cation exchange chromatography, ethanol precipitation, affinity chromatography and high performance liquid chromatography (HPLC). The particular method used will depend upon the properties of the polypeptide and the selection of the host cell; appropriate methods will be readily apparent to those skilled in the art.

The present invention also relates to antibodies which bind a polypeptide which is a caspase present in immature thymocytes and necessary for apoptosis. For instance, polyclonal and monoclonal antibodies, including non-human and human antibodies, humanized antibodies, chimeric antibodies and antigen-binding fragments thereof (*Current Protocols in Immunology*, John Wiley & Sons, N.Y. (1994); EP Application 173,494 (Morrison); International Patent Application WO86/01533 (Neuberger); and U.S. Pat. No. 5,225, 539 (Winters)) which bind to the described caspase are within the scope of the invention. A mammal, such as a mouse, rat, hamster or rabbit, can be immunized with an immunogenic form of the caspase (e.g., the caspase or a peptide comprising an antigenic fragment of the caspase which is capable of eliciting an antibody response). Techniques for conferring immunogenicity on a protein or peptide include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, polyclonal antibodies can be isolated from the serum. Monoclonal antibodies can also be produced by standard techniques which are well known in the art (Kohler and Milstein, *Nature* 256:495–497 (1975);

Kozbar et al., *Immunology Today* 4:72 (1983); and Cole et al., *Monoclonal Antibodies and Cancer Therapy*, Alan R. Liss, Inc., pp. 77–96 (1985)). The term "antibody" as used herein is intended to include fragments thereof, such as Fab and F(ab)$_2$. Antibodies described herein can be used to inhibit the activity of the caspase described herein, particularly in vitro and in cell extracts, using methods known in the art. Additionally, such antibodies, in conjunction with a label, such as a radioactive label, can be used to assay for the presence of the expressed protein in a cell from, e.g., a tissue sample, and can be used in an immunoabsorption process, such as an ELISA, to isolate the caspase. Tissue samples which can be assayed include human tissues, e.g., differentiated and non-differentiated cells. Examples include bone marrow, thymus, kidney, liver, brain, pancreas, fibroblasts and epithelium.

The present invention also pertains to pharmaceutical compositions comprising polypeptides described herein. For instance, a polypeptide or protein, or prodrug thereof, of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to well known procedures, and will depend on the ultimate pharmaceutical formulation desired. Methods of introduction of exogenous peptides at the site of treatment include, but are not limited to, intradermal, intramuscular, intraperitoneal, intravenous, subcutaneous, oral and intranasal. Other suitable methods of introduction can also include gene therapy, rechargeable or biodegradable devices and slow release polymeric devices. The pharmaceutical compositions of this invention can also be administered as part of a combinatorial therapy with other agents.

The biochemistry of enzyme activation for other caspases has been discussed. In the case of the cell surface receptors CD95 and TNFR-1, cytoplasmic proteins which interact with the death domains of these transmembrane proteins have been identified: these include a TNFR1-associated death domain protein (TRADD) (Hsu et al., *Cell* 81:495–504 (1995)), a Fas-associated death domain protein (FADD) (Chinnaiyan et al., *Cell* 81:505–512 (1995); Boldin et al., *J. Biol. Chem.* 270:7795–7798 (1995)) and a receptor interacting protein (RIP) (Stranger et al., *Cell* 81:513–523 (1995)). FADD appears to function as a common signalling component of both TNFR-1 and CD95 (Chinnaiyan et al., *J. Biol. Chem.* 271:4961–4965 (1996b); Hsu et al.; *Cell* 84:299–308 (1996a)), while TRADD mediates the interaction of TNFR-1 with FADD to induce apoptosis (Hsu et al., *Cell* 84:299–308 (1996a)). RIP appears to be involved in NFkB signalling (Hsu et al., *Immunity* 4:87–396 (1996b)). Upon oligomerization of CD95 or TNFR1, these cytoplasmic adapter molecules are recruited to the receptor cytoplasmic domain to form a death induced signalling complex or DISC (Kischkel et al., *EMBO J.* 14:5579–5588 (1995)). The recent cloning of FLICE (MACH, Mch5, caspase-8) (Muzio et al., *Cell* 85:817–827 (1996); Boldin et al. (1996); Fernandes-Alnemri et al. (1996)), also recruited to the DISC (Muzio et al. (1996)), links the cell surface death receptors directly to the initiation of a cascade of caspase activation: FLICE is recruited to the DISC and binds the Death Effector Domain (DED) of FADD. Upon receptor oligomerization, FLICE is cleaved to produce an active caspase. Thus, the initial step of caspase activation after death receptor ligation has been defined for CD95 and TNFR1 (Muzio et al. (1996); Boldin et al. (1996)).

The anti-CD3ε mAb-induced deletion of DP thymocytes was also blocked by zVADfmk in FTOC, suggesting that the same caspase involved in peptide/MHC-triggered death is active in this apoptotic pathway. However, cross-linking with this antibody did not induce deletion of DP thymocytes to the same extent as did peptide/MHC. It might be expected that crosslinking with anti-CD3ε mAb would be more extensive than that induced by peptide/MHC, since there are two CD3ε molecules per TCR and only one binding site for peptide/MHC. Furthermore, the mAb is bivalent, unlike the peptide/MHC, which is monovalent. The most likely explanation for this apparent paradox is that peptide/MHC-induced triggering may recruit other molecules, which act in synergy to provide a more potent death signal than that exclusively provided by crosslinking of TCR molecules by mAb.

For example, peptide/MHC binding recruits the CD4 or CD8 co-receptor with the attendant activation of protein tyrosine kinases including p56lck (reviewed in Rudd, *Immunol. Today* 11:400–406 (1990)). Furthermore, other signalling molecules have been shown to affect negative selection as discussed herein, although their roles in activation of the caspase remain to be determined. Certainly, there is precedent for the role of dual signalling within the T cell lineage: activation of resting peripheral T cells requires TCR crosslinking as well as co-stimulation through CD28 and its ligands, B7-1 and B7-2 (reviewed in Bluestone, J. A., *Immunity* 2:555–559 (1995)). Apoptosis of peripheral T cells involves second signals through Fas (CD95) and Fas-ligand, the expression of which are regulated by TCR signalling (Crispe, I. N., *Immunity* 1:347–349 (1994)). Such dual signalling may also play a role in thymic selection; a second signal derived from thymic stroma along with the specificity-determining TCR/peptide/MHC interaction may be required for negative selection (Page et al., *J. Immunol.* 151:1868–1880 (1993); Degermann et al., *J. Immunol.* 152:3254–3263 (1994); Punt et al., *J. Exp. Med.* 179:709–713 (1994); Lerner et al., *EMBO J.* 15:5876–5877 (1996)). For example, CD40L is induced on activated thymocytes (Foy et al., *J. Exp. Med.* 182:1377–1388 (1995)) and CD40 is expressed in thymic stroma (Galy and Spits, *J. Immunol.* 149:775–782 (1992)). Injection of anti-CD40L mAb resulted in defective deletion of thymocytes and inhibited medullary B7-2 expression (Foy et al. (1995)). CD40-CD40L interactions may affect negative selection, primarily by induction of new signalling molecules on the thymic stromal cell surface. Targeted disruption of CD30, another member of the TNF receptor family, produces a phenotype suggestive of a defect in negative selection (Amakawa et al., *Cell* 84:551–562 (1996)). Thus, receptor-ligand interactions between thymocytes and stromal cells may induce one or more additional signals from the stroma important in the modulation of negative selection.

Glucocorticoids induce deletion of DP thymocytes in FTOC of C57BL/6 mice, and this deletion is blocked by zVADfmk. Rat thymocytes in suspension also undergo glucocorticoid-induced death which is blocked by zVADfmk (Fearnhead et al., *FEBS Lett.* 375:283–288 (1995)). This death pathway is inhibited by Bcl-2 in contrast to that of negative selection (reviewed in Yang and Korsmeyer (1996)). Since both forms of DP thymocyte depletion are blocked by zVADfmk, while Bcl-2 selectively affects glucocorticoid-induced deletion but does not alter negative selection, it appears that the glucocorticoid and antigen/

MHC pathways share some, but not all, components of the death pathway. Nevertheless, they converge to a common death effector mechanism involving a thymic caspase.

In the immune system, apoptosis plays a critical role in the development and maintenance of mature lymphocytes. In peripheral T-cells, CD95 and its ligand are induced during the development of an immune response (Ju et al., *Nature* 373:444–448 (1995)); thus apoptosis mediated by the CD95 pathway serves to limit and control T-cell activation. The CD95 pathway has been relatively well characterized as described above and involves, at a minimum, activation of caspase-1, caspase-3, caspase-7 and caspase-8. Activation of target cell caspase-3, caspase-8 and ICH-3 by cytotoxic T cells, as noted above, is also an important element of immune effector function within the peripheral lymphoid organs. The present findings add the process of negative selection to the expanding role of caspases in immune regulation.

It is a long-standing enigma as to how events which induce negative selection and death in immature thymocytes induce activation and accompanying proliferation in mature T cells (Ramarli et al., *Proc. Natl. Acad. Sci. USA* 84:8598–8602 (1987); Kappler et al., *Cell* 49:273–230 (1987)). Hence, the developmental stage of the T cell determines its response to a particular stimulus. In TCR transgenic mice, antigenic peptides which activate peripheral T cells to proliferate trigger depletion of the immature thymocytes bearing the identical TCR (Fowlkes and Pardoll (1989)). Most TCR transgenic models in which deletion by peptide antigen has been examined demonstrate that the deletion involves the immature DP thymocytes (Murphy et al. (1990); Vasquez et al., *J. Exp. Med.* 175:1307–1316 (1992); Sebzda et al. (1994); Ashton-Rickardt et al., *Cell* 76:651–663 (1994a); Hogquist et al., *Cell* 76:17–27 (1994)). The presence of the peptide/MHC activated caspase in the DP thymocyte subset further identifies this population as the one in which negative selection is operative.

Interactions between peptide/MHC expressing antigen presenting cells and DP thymocytes is also required for positive selection. Thymocyte expressing TCRs which productively bind MHC-peptide ligands on thymic stromal cells selectively receive signals to mature into functional single positive (SP) cells (Berg et al., *Cell* 60:1043–1053 (1990); Koller et al., *Science* 248:1227–1230 (1990)). MHC-bound cognate peptides which interact with TCRs with high affinity induce negative selection, while peptides containing a single amino acid substitution, which lowers the affinity for the TCR without affecting MHC binding (altered peptide ligands, APL's), induce positive selection (Hogquist et al. (1994); Jameson et al., *Nature* 369:750–752 (1994); Spain et al., *J. Immunol.* 152:1709–1717 (1994); Hogquist et al., *Immunity* 3:79–86 (1995)). In addition, cognate peptides, when present at a very low concentration, can induce positive rather than negative selection (Sebzda et al. (1994); Ashton-Rickardt et al., *Cell* 76:651–663 (1994a)), supporting the notion of an avidity model to explain thymic selection outcome (Ashton-Rickardt et al., *Immunol. Today* 15:362–366 (1994b)). Some studies suggest that negative and positive selection are separated spatially and temporally, and that positive selection precedes negative (Laufer et al., *Nature* 383:81–85 (1996)). Others have suggested that both forms of selection may occur concurrently but that only a single outcome results.

The question of what determines the fate of a thymocyte facing the pathways of positive versus negative selection remains unclear. Certainly, the strength of a signal induced by the extent of receptor crosslinking can vary and be modulated by ligand affinity and receptor occupancy (Meuer et al., *Proc. Natl. Acad. Sci. USA* 81:1509–1513 (1984); Maruyama et al., *Cell* 48:343–350 (1987)). For example, the activity of the IL2 and IL2R promoters are differentially induced, depending on the degree of TCR crosslinking in Jurkat T cells (Maruyama et al. (1987)). Both Ca2+ flux and protein phosphorylation triggered by cell surface receptors are variably affected by the degree of TCR crosslinking (Alcover et al., *Proc. Natl. Acad. Sci. USA* 83:2614–2618 (1986); Koyasu et al., *Proc. Natl. Acad. Sci. USA* 91:6693–6697 (1994)). Such events regulate many cellular processes; thus, the different intensities of interaction between a TCR and its ligand may induce very different outcomes on the same thymocytes. In this way, it may be possible for the thymus to filter out those autoreactive T cells with highest TCR affinity for self-MHC peptide, while retaining thymocytes with weak, but nevertheless self-MHC restricted, specificities. This process of thymocyte "editing" is probably dependent on more parameters than the TCR-pMHC interaction itself, and, therefore, influenced by co-receptor interactions as well. The latter offers an explanation for why the level of co-receptor expression alters the outcome of selection (Robey et al., *Cell* 69:1089–1096 (1992)).

Recently, using N15 TCRtg RAG-2-/- H-$2^b$ mice, a population of DP TCR-high thymocytes which is resistant to deletion by peptide antigen was identified. Presumably, these thymocytes have already been positively selected by an endogenous peptide antigen (APL) prior to VSV8 injection and are on their way to becoming mature CD8 SP T cells. If the activation of a caspase is the mechanism by which negative selection operates, then these cells must be unable to activate the thymic caspase upon TCR engagement with VSV8. It may be that the caspase mRNA is expressed only at a limited stage of development, and these cells no longer express the caspase gene. Alternatively, these cells may produce an inhibitor of the thymic caspase, such as a Bcl-2-like molecule, which inactivates the thymic caspase. In addition, a molecule which provides a second signal(s) necessary for thymic selection as discussed above may no longer be expressed on the DP thymocytes. Once the genetic and biochemical details of the negative selection pathway are defined, it should be possible to determine which of these mechanisms accounts for the escape of the DP TCR-high thymocytes from peptide/MHC induced death.

Accordingly, the work described herein has many uses. For example, it is apparent from this work that apoptosis can be inhibited in lymphocytes, particularly immature thymocytes, by inhibiting the activity of the caspase implicated herein in programmed cell death. As used herein, "inhibition" is intended to encompass any reduction in the occurrence of apoptosis, including complete abolishment of apoptosis. Inhibition of caspase activity can be brought about by decreasing either the amount of caspase enzyme present, the enzymatic activity of the caspase enzyme, or both. For example, the activity of the caspase enzyme described herein can be inhibited by a tripeptide or tetrapeptide having an amino acid sequence of VAD, YVAD and DEVD, for example, and wherein the tetrapeptide or tripeptide is linked to a fluoromethylketone, an acyloxymethylketone, a chloromethylketone, a diazomethylketone, an aldehyde, a semicarbazone, a nitrile or an epoxide. These compounds reversibly or irreversibly react with the active site cysteine thiol of the cysteine protease. A compound of this type, or a pro-drug thereof, can be administered to an individual to inhibit the activity of the caspase implicated in cell death, thereby inhibiting apoptosis.

By inhibiting apoptosis as described above, the down regulation of lymphocytes, particularly thymocytes, can be prevented or inhibited; thus, DP thymocytes are prevented from self-destruction. This results in a T cell receptor population with an increased proportion of autoreactive T cells; that is, there is an increased occurrence of T cells which have specificity for the host animal's own cells. This is particularly advantageous when it is desirable to generate an immune response against the host's own cells (an autoimmune response), such as, for example, in the case of tumor growth and cancers such as leukemia and melanomas. This technology is especially useful for preparing animal models having depleted T cell populations and animal models for autoimmune disease. The invention also pertains to methods of enhancing an immune response against an antigen in a mammal by administering to the mammal an effective amount of an agent which inhibits the activity of the caspase along with the selected antigen. In a particular embodiment, the antigen is a cancer antigen.

Many uses of the technology will be apparent to the skilled artisan. For example, an appropriate animal, e.g., a mammal, can be immunized with a selected self-antigen (e.g., tumor antigen or other protein present on the surface of the targeted cell or tissue) concurrently with treatment with a caspase-inhibitor; thus, T cells are generated which recognize the self-antigen and are not destroyed by the caspase activity. These self-recognizing T cells have the capacity to mount an immune response to the self-antigen in the animal, thereby destroying the targeted cell or tissue.

This invention pertains to methods of enhancing the activity of the caspase enzyme, thereby enhancing apoptosis of self-recognizing T cells. As used herein, "enhancing" is intended to encompass any increase in caspase activity, whether brought about by increase in the activity of the enzyme itself, or by increase in the amount of enzyme or enzyme mimic present, or both. As used herein, "enzyme mimic" is intended to mean an agent which has the same activity as (or mimics) the caspase and includes fragments or other variants of the caspase as described above.

Disorders can be treated by altering the specific programmed cell death of autoreactive T cells which are responsible for the autoimmune disorder. For example, the invention pertains to methods of enhancing apoptosis in immature thymocytes by contacting the thymocytes, or active derivatives or fragments thereof, with an agent which enhances caspase activity. The caspase activity can be enhanced in an animal to produce a depleted T cell population; this is particularly advantageous in instances where the animal's T cells have developed harmful specificities, e.g., rheumatoid arthritis and juvenile diabetes melitis. In such situations, the naturally-occurring caspase of the harmful cell is triggered with an appropriate agent, e.g., an antigen or drug or agent which causes or enhances caspase activity, to cause apoptotic death of the cell. It is also contemplated that cells, particularly thymocytes, which, in nature, lack caspase and/or procaspase expression and activity can be engineered to express the caspase and/or procaspase of the invention by gene therapy methods. For example, DNA encoding the caspase or procaspase protein, or an active fragment or derivative thereof, can be introduced into an expression vector, such as a viral vector, and the vector can be introduced into appropriate cells which lack caspase and/or procaspase expression in an animal. In such a method, an immature thymocyte population can be engineered to inducibly or constitutively express active caspase, eliminating the need for the cell to convert inactive procaspase to caspase to induce apoptosis. In a preferred embodiment, the vector is delivered to the bone marrow, for example as described in Corey et al. (*Science* 244:1275–1281 (1989)).

Enhancement or inhibition of apoptosis of self-recognizing lymphocytes as described above can be useful in the treatment of acute and chronic immune and autoimmune diseases, including chronic hepatitis, systemic lupus erythematosus, rheumatoid arthritis, thyroidosis, scleroderma, diabetes mellitus, Graves' disease, Beschet's disease and graft versus host disease (graft rejection).

Thus, the present invention can be used to treat a range of disorders in addition to the above immune and autoimmune diseases; for example, various infections, including, but not limited to, sepsis syndrome, cachexia, circulatory collapse and shock resulting from acute or chronic bacterial infection, acute and chronic parasitic and/or infectious diseases from bacterial, viral or fungal sources, such as a HIV, AIDS (including symptoms of cachexia, autoimmune disorders, AIDS dementia complex and infections) can be treated. Inflammatory diseases, such as chronic inflammatory pathologies and vascular inflammatory pathologies, including chronic inflammatory pathologies such as sarcoidosis, chronic inflammatory bowel disease, ulcerative colitis, and Crohn's disease and vascular inflammatory pathologies, such as, but not limited to, disseminated intravascular coagulation, atherosclerosis, and Kawasaki's pathology are also suitable for treatment by methods described herein.

Treatable disorders also include neurodegenerative diseases, including, but not limited to, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo palsy; Cerebellar and Spinocerebellar Disorders, such as astructural lesions of the cerebellum; spinocerebellar degenerations (spinal ataxia, Friedreich's ataxia, cerebellar cortical degenerations, multiple systems degenerations (Mencel, Dejerine-Thomas, Shi-Drager, and MachadoJoseph)); and systemic disorders (Refsum's disease, abetalipoprotemia, ataxia, telangiectasia, and mitochondrial multi system disorder); demyelinating core disorders, such as multiple sclerosis, acute transverse myelitis; disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, or any subset thereof.

It is also recognized that malignant pathologies involving tumors or other malignancies, such as, but not limited to leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or Mycosis fungoides)); carcinomas (such as colon carcinoma) and metastases thereof; cancer-related angiogenesis; infantile hemangiomas; alcohol-induced hepatitis. Ocular neovascularization, psoriasis, duodenal ulcers, angiogenesis of the female reproductive tract, can also be treated.

The present invention also relates to an assay for identifying agents which alter the activity of the caspase implicated in lymphocyte, particularly thymocyte, apoptosis. For example, the caspase or procaspase, or an active fragment or derivative thereof, can be contacted with a caspase substrate in the presence of an agent to be tested, and the level of lymphocyte apoptosis can be assessed; alternatively, the level of lymphocyte apoptosis can be assessed and compared with the corresponding level in a control in the absence of the agent to be tested. The caspase can be contacted directly with the substrate in the presence of the agent to be tested, or a thymocyte or cell lysate thereof comprising the caspase or procaspase can be contacted with the agent to be tested. Enhancement of apoptosis, or an increase in the level of apoptosis relative to a control, indicates that the agent is an agonist of caspase activity. Examples of caspase enhancing agents or agonists include, for example, compounds or enzymes which will convert procaspase to caspase, enhance oligomerization of the caspase, or an enzymatically active fragment or variant thereof, a sequence which encodes one of the above in an appropriate expression vector or a compound which will enhance the expression of the procaspase or caspase in the cell. Similarly, inhibition of apoptosis, or a decrease in the level of apoptosis relative to a control, indicates that the agent is an antagonist of caspase activity. Examples of caspase antagonists include, for example, compounds or enzymes which will inhibit conversion of procaspase to caspase, inhibit oligomerization of the caspase, or a variant or caspase without enzymatic activity which can inhibit (e.g., by competitive inhibition) caspase activity, decrease or eliminate expression of active procaspase or caspase in the cell.

The present invention also relates to agents identified by the assay described above. Agents identified by the assay described herein may enhance (e.g., prolong or increase) or inhibit (e.g., shorten or decrease) the activity of the caspase implicated in apoptosis. Agents which can inhibit caspase activity can be selected from tripeptide or tetrapeptide having an amino acid sequence of VAD, YVAD, or DEVD, and wherein the tetrapeptide or tripeptide is linked to a fluoromethylketone or an acyloxymethylketone, or a prodrug thereof.

The following Examples are offered for the purpose of illustrating the present invention and are not to be construed to limit the scope of this invention. The teachings of all references cited herein are hereby incorporated herein by reference.

EXAMPLES

Materials and Methods

T Cell Receptor Constructs

The full-length N15α and N15β cDNAs were isolated by oligonucleotide priming from total RNA of the N15 CTL clone and subcloned into the pCRII vector (Invitrogen). To engineer N15 constructs for the creation of transgenic mice, TCR shuttle vectors were used (kindly provided by M. Davis). A PCR product encoding the N15 Vα8-Jα5 was generated from 50 ng of psTCR$_{N15LZ\alpha}$ using 1.64 µg of each of the following oligonucleotides:

5'-CTCGAGACCTGTGTGGATTAAAAAC-CTCTCTGATTCTGGTTTGCTTTTCTGTTTCC AAG-CAGGGGTGAGAGGAGACTCCGTGACCCA-GACAGAAGGCCTG-3, (SEQ ID NO: 5); and 5'-GCGGCCGCTTGGGCCCAAGAAACTGT-CATCAAACGTACGTGCTATAACCTTCAGTC TGG-TACCTGCTCC-3' (SEQ ID NO: 6).

Only 10 cycles of PCR (1' at 94° C., 1' at 60° C. and 1' at 72° C.) were performed on the relative large amount of template DNA to minimize the probability of mutation. The resulting 448 bp fragment was digested with XhoI and NotI and inserted into the similarly digested TCRα shuttle vector. The N15 TCRβ expression vector was generated by ligation of a 423 bp ClaI/NotI digested PCR product derived from the psTCR$_{N15LZ\beta}$ (same PCR conditions as described above for N15$_\alpha$) encoding N15 Vβ5.2-Dβ2-Jβ2, 6 into the ClaI/NotI sites of the TCRβ shuttle vector. The following oligonucleotides were used to amplify the N15β fragment: 5'-ATCGATTCCCCTTCTTGTCTGTATTTA-CATCTTTTGTTTTCTTCTCTTCTAGGATC AGCAGAT-TCTGGGGTTGTCCAGTCTCCAAG-3' (SEQ ID NO: 7); and 5'-GCGGCCGCACGTGGGGCCCCAGCTCAC-CTAAAACCGTGAGCCTGGTGCCGGGACC G-3' (SEQ ID NO: 8).

All the oligonucleotides contained restriction sites in the 5' end. The cDNA inserts encoding VJ and V(D)J sequences in N15 α and β shuttle constructs respectively were sequenced and found to be error-free.

Transgenic Mice

The N15 α and β shuttle constructs were digested with ClaI/SalI or PvuI/SalI, respectively, leaving the bacterial vector sequences attached to the T cell receptor gene. These DNAs were co-injected into [SJL×C57BL/6]F2 or RAG-2$^{-/-}$ [43] fertilized eggs and implanted into foster mothers. Resulting progeny mice were screened for integration of the N15 α and β chain DNA by Southern blot analysis of tail DNA and by FACS analysis of N15β chain expression in peripheral blood nucleated cells. Four transgenic founders were identified, two for each background. Progeny of line L2 (RAG-2$^{-/-}$ background), backcrossed for 2–5 generations into C57BL/6-RAG-2$^{-/-}$ mice, were used for the experiments described below. RAG-2$^{-/-}$ and βRAG-2$^{-/-}$ backcrossed for 6–10 generations into C57BL/6, as well as the N15tg lines, were maintained and bred under sterile barrier standard conditions in the animal facility of Dana Farber Cancer Institute.

C57BL/6 mice were purchased from Taconic (Germantown, N.Y.) For injection of anti-CD3ε specific hamster anti-mouse mAb 145-2C11 (2C11), the anti-CD3ε mAb (American Type Culture Collection, Rockville, Md.) was purified by standard procedures (Coligan et al., Current Protocols in Immunology, John Wiley & Sons (1994)), and 200 mg was injected intraperitoneally in PBS. For injection of peptide, 24 mg of VSV8 (RGYVYQGL; SEQ ID NO: 9) or SEV9 (FAPGNYPAL) was injected in 100 ml PBS into the tail vein of the mouse.

Fetal Thymic Organ Culture (FTOC)

Fetuses of C57BL/6 mice were dissected at day 14.5 of pregnancy, with the day of the vaginal plug counted as day 1. Fetuses of N15 TCRtg RAG-2$^{-/-}$ H-2$^b$ mice were dissected at day 15.5. Fetal lobes were removed and cultured in 6-well Transwell dishes (Costar, Kennebunk, Me.) using 1.6 ml of complete DMEM-10 (Life Technologies, Gaithersburg, Md.) as described in Coligan, et al. (1994). The samples were incubated in a humidified atmosphere with 5% $CO_2$ for 4–5 days at 37° C. and treated with specific reagents as described. For harvesting, lobes were ground between frosted glass slides in PBS-1% BSA, washed, and used for flow cytometric analysis (FACS analysis).

Flow Cytometric Analysis

Monoclonal antibodies used were R-phycoerythrin (PE) labeled anti-CD4 (H129.19) and Red613 labeled anti-CD8

(53-6.7) (GIBCO BRL, Grand Island, N.Y.). Harvested thymocytes were washed and stained for 30 minutes with anti-CD4 and anti-CD8 mAbs. Flow cytometric analysis was performed on a FACScan (Becton Dickinson, San Jose, Calif.). Samples were gated on live cells based on forward and side scatter parameters. Data on 10,000 events per sample were collected in list mode using FACScan Research software and analyzed using LYSYSII software (Becton Dickinson, San Jose, Calif.).

Synthesis of Peptide-Based Inhibitors and Related Compounds

N-benzyloxycarbonyl-Val-Ala-Asp-fluoromethylketone, b-methyl ester (zVADfmk) was from Enzyme System Products (Dublin, Calif.). Biotin-YVADamk was purchased from Amersham Life Science (Arlington Heights, Ill.).

N-[Biotinylaspartyl(b-t-butyl ester)glutamyl(g-t-butyl ester)valine was prepared by solid phase synthesis on a 2-chlorotrityl resin (Barlos et al., *Intl. J. Pept. Protein Res.* 37:513–520 (1991)) using an HOAt/HATU coupling protocol (Carpino et al., *J. Chem. Soc., Chem. Commun.* 201–203 (1994)). Acyloxyketone, N-Z-aspartic acid[(2,6-dimethylbenzoyl)oxy]-methyl ketone, b-t-butyl ester, was prepared according to the method of Krantz (Krantz et al., *Biochemistry* 30:4678–4687 (1991)) from the corresponding bromomethyl ketone (Dolle et al., *J. Med. Chem.* 37:563–564 (1994a)) and deprotected by hydrogenolysis (Dolle et al., *J. Med. Chem.* 37:3863–3866 (1994b)) to afford aspartic acid [(2,6-dimethylbenzoyl)oxy]methyl ketone, b-t-butyl ester, as the HCl salt. Coupling of this amine with N-[biotinylaspartyl(b-t-butyl ester)glutamyl(g-t-butyl ester)valine was carried out by HOAt/HATU-mediated solution phase synthesis (Carpino (1993)) as follows:

N-(Biotinylaspartylglutamylvalinyl)aspartic acid [(2,6-Dimethylbenzoyl)oxy]methyl Ketone [Biotin-DEVDamk]

Diisopropylethyl amine (110 µL, 0.645 mmol) was added to an ice-cooled solution of N-[biotinylaspartyl(b-t-butyl ester)glutamyl(g-t-butyl ester)valine (150 mg, 0.215 mmol), aspartic acid[(2,6-dimethylbenzoyl)oxy]methyl ketone, b-t-butyl ester hydrochloride (80 mg, 0.215 mmol), HOAt (30 mg, 0.215 mmol) and HATU (125 mg, 0.33 mmol) in DMF (1 mL), and the resulting solution was allowed to warm to room temperature. After stirring overnight, the mixture was concentrated under reduced pressure, and the residue was chromatographed on a silica gel column eluting with chloroform followed by chloroform/methanol (20:1). The material was further purified by a second silica gel column eluting with chloroform followed by a gradient of chloroform/acetone/methanol (4:1:0)-(2:1:0)-(2:1:1%) to produce 60 mg of the coupled product as a colorless solid. The tert-butyl esters were removed by treating this material with a mixture of TFA/DCM (3:2, 2.5 mL) at room temperature for 3 hours. Concentration under reduced pressure, followed by repeated treatment (3×) with toluene (0.5 mL) and concentration, produced 50 mg (quant) of the desired product as a light yellow solid. Recrystallization from methanol gave pure product which was shown by reverse phase HPLC (C18) analysis to consist of a 1:1 mixture of diastereoisomers. Similar to the observation of Thornberry (Thornberry et al., *Biochemistry* 33:3934–3940 (1994)), 1H NMR analysis indicated the diastereomeric center to be at the $P_1$ aspartic acid a-carbon. ES mass spectrum (M−) m/e 847 [M−H], 869 [M−H+Na]; ES mass spectrum (M+) m/e 849 [M+H], 871 [M+Na]

N-(Z-Valinylalanyl)Aspartic Acid Methyl Ketone, b-Methyl Ester [z-VADmk]

N-(Z-Valinylalanyl)aspartic acid methyl ketone, b-methyl ester [z-VADmk] was prepared as a diastereomeric mixture (racemic at aspartyl a-carbon) from N-(Z-valinylalanyl) aspartic acid, b-methyl ester (standard solid phase coupling) by a Dakin-West reaction with acetic anhydride, triethylamine and DMAP at 50° C. (Steglich and Hofle., 1969). FAB mass spectrum (M+) m/e 450 [M+H].

Immunohistologic Analysis and Tunel Assay

Fetal thymuses were embedded in O.C.T. compound (Miles, Elkhart, Ind.) on dry ice. Four mm sections were prepared and subsequently stored at −80° C. For the TUNEL assay, frozen tissue sections were fixed in 3% buffered formalin for 10 minutes at room temperature. After washing with PBS, sections were fixed again in ethanol/acetic acid (2:1) for 10 minutes at −20° C. Endogenous peroxidase activity was blocked by covering the sections with 0.5% $H_2O_2$ for 20 minutes at room temperature. The sections were rinsed with PBS and immersed in TdT buffer (30 mM Trizma base, pH 7.2, 140 mM sodium cacodylate, 1 mM cobalt chloride). The sections were incubated with 2–4 mM biotinylated dUTP (Boehringer Mannheim, Mannheim, Germany) and 5–10 U TdT (Promega, Madison, Wis.) in 25 ml TdT buffer in a humid atmosphere at 37° C. for 2 hours. The reaction was terminated by transferring the slides to TB buffer (300 mM NaCl, 30 mM Na citrate) for 15 minutes. After a PBS rinse, sections were incubated with 2% BSA for 10 minutes, rinsed in PBS for 5 minutes, incubated with avidin/biotinylated-peroxidase complex (Dako, Santa Barbara, Calif.) diluted 1:100 in PBS for 30 minutes, washed in PBS and developed with 3-amino-9-ethylcarbazole (Aldrich, Milwaukee, Wis.). Sections were lightly counterstained with Meyer's hematoxin (Gavrieli et al., *J. Cell. Biol.* 119:493–501 (1992)).

Two-color immunohistochemical analysis was performed as previously described (Mizoguchi et al., *J. Exp. Med.* 183:847–856 (1996)). Briefly, 4 mm thick specimens were fixed in acetone for 7 minutes, air dried, and incubated with purified anti-CD4 antibody (clone L3T4, PharMingen, San Diego, Calif.) for 1 hour at room temperature. Specimens were incubated for 30 minutes with 0.3% hydrogen peroxide in PBS to block endogenous peroxidase activity. Endogenous biotin was blocked by sequential incubations with avidin-D (Vector, Burlingame, Calif.) and d-biotin (Sigma, St. Lous, Mo.). For detection, biotinylated rabbit anti-rat Ig (Vector) was used, followed by an optimal dilution of avidin-biotinylated peroxidase complex (Dako). The specimens were developed in a solution of 3-amino-9-ethylcarbazole (Aldrich) and the reaction stopped by dipping in distilled water for 5 minutes and washing in PBS (pH 7.4) for 10 minutes. The specimens were then incubated with biotin-DEVDamk peptide at room temperature for 1 hour, followed by incubation with ABC-alkaline phosphatase reagent (Vector, Burlingame, Calif.) for 30 minutes. After 15 minutes of development with alkaline phosphatase substrate Kit III (Vector) and 1M levamisole (Sigma, St. Louis, Mo.), the specimens were postfixed with 2% paraformaldehyde and mounted with glycergel (Dako, Carpinteria, Calif.).

PREPARATION OF THYMIC LYSATES AND WESTERN BLOT ANALYSIS

Thymocyte suspensions were prepared as described above for FACS. Cells were washed three times in PBS-1 BSA, and lysates were prepared as previously described (Thornberry et al. (1994)). Briefly, thymocytes were resuspended at $1 \times 10^8$/ml in hypotonic buffer containing 25 mM Hepes, pH 7.5, 5 mM $MgCl_2$, 1 mM EGTA, 1 mM PMSF, 10 mg/ml leupeptin and 10 mg/ml pepstatin. After 20 minutes on ice, cells were broken with 20 strokes in a tight-fitting Dounce homogenizer. Cell lysates were clarified by centrifugation at 2000 rpm in an eppendorf microfuge for 10 minutes, followed by an 8 minute spin in a Beckman airfuge at 100,000 g. The lysates were dialyzed overnight at 4° C. against 20 mM Tris, pH 7.8, 2 mM DTT and 0.1 CHAPS. Cell lysates were aliquoted and stored at −80° C. Recombinant Yama and Mch2a were prepared as described (Orth et al., *J. Biol. Chem.* 271:20977–20980 (1996)).

For Western blot analysis, cell lysate equivalent to $2\times10^5$ cells was incubated with the indicated additions for 15 minutes at 25° C. Non-reducing sample buffer was added, samples boiled for 7 minutes and run on 12.5% SDS-PAGE under nonreducing conditions. Gels were blotted onto nitrocellulose and the membranes blocked overnight in PBS, 3% BSA, 0.1% Tween-20. The filter was washed twice for 10 minutes in PBS, 0.1% BSA, 0.1% Tween-20 and incubated 2 hours at room temperature with a 1:10,000 dilution of streptavidin-conjugated horseradish peroxidase (ICN, Costa Mesa, Calif.) in PBS, 0.1% BSA, 0.1% Tween-20. The filter was washed 6 times for 10 minutes with 50 mM Tris-HCl, pH 7.5, 0.25% gelatin, 0.05% Tween-20, 150 mM NaCl, 5 mM EDTA, then washed once in PBS and developed by ECL (Renaissance, NEN, Boston, Mass.).

Results

Caspase Inhibition in FTOC Prevents DP Thymocyte Deletion Mediated by ANTI-CD3ϵ mAb Prior studies utilizing the anti-CD3ϵ specific hamster anti-mouse mAb 145-2C11 (2C11) have shown that DP thymocytes are susceptible to undergo apoptotic cell death upon exposure to 2C11 in FTOC (Smith et al., *Nature* 337:181–184 (1989)) or upon parenteral in vivo administration (Shi et al., *J. Immunol.* 146:3340–3346 (1991)). Therefore, the effect of a caspase inhibitor on anti-CD3ϵ-induced deletion of the CD4+ CD8+DP thymocytes was first analyzed using C57BL/6 animals. Fetal thymocytes were dissected on day 14.5 of pregnancy and cultured in transwells for 4 days. On day 4, additions were made to the FTOCs, including 2C11 mAb in the presence or absence of 100 mM zVADfmk, an irreversible inhibitor of cysteine proteases, and thymocytes were harvested 18 hours later.

Upon 2C11 mAb addition, the percent of DP thymocytes is reduced from 66% in the control culture to 37% in the culture treated for 18 hours with 200 mg/ml 2C11 mAb. Moreover, the deletion of these DP thymocytes is inhibited by a 2-hour preincubation with zVADfmk. zVADfmk alone does not alter the percentage of DP thymocytes nor does dimethyl sulfoxide (DMSO), the additive used to solubilize zVADfmk, affect the deletion of DP thymocytes. A control hamster anti-mouse mAb, H28 (Becker et al., *Cell* 58:911–921 (1989)), directed against a segment of the TCR a chain which is inaccessible on intact thymocytes, has no effect on the FTOC.

zVADfmk Inhibits Glucocorticoid-Induced DP Thymocyte Death in FTOC

DP thymocytes are exquisitely sensitive to pharmacological doses of glucocorticoids in vivo (Wyllie, *Nature* 284:555–556 (1980)). The rapid thymic involution known to result from stress is a consequence, in large part, of endogenous release of steroids as well. To determine whether caspase inhibition blocks DP thymocyte apoptosis induced by corticosteroids, the effects of dexamethasone on DP thymocyte survival in FTOC were examined in the presence or absence of zVADfmk.

Dexamethasone at 0.1 mM reduces the percentage of DP thymocytes from 74% to 19%. A 2-hour pretreatment with 100 mM zVADfmk protects the CD4+ CD8+population from dexamethasone-induced death. The inhibition of deletion is specific to the zVADfmk reagent and not due to the DMSO solvent. These results demonstrate that two well-known inducers of CD4+ CD8+DP thymocyte death, anti-CD3ϵ mAb and glucocorticoids, are blocked by inhibition of cysteine protease activity.

zVADfmk Protects DP Thymocytes from Antigen-Induced Deletion in N15 TCR tg RAG-$2^{-/-}$ H-$2^b$ Mice Given that negative selection of thymocytes in vivo is antigen-driven, the effect of zVADfmk on specific peptide-induced deletion of DP thymocytes in FTOC derived from TCR tg mice was tested. To this end, the N15 TCR tg mouse was employed; this mouse bears a class I MHC-restricted TCR and recognizes the vesicular stomatitis virus nuclear protein octapeptide VSV8 in the context of H-2 Kb. The VSV8 peptide interacts with Kb with high affinity such that a single in vitro or in vivo exposure efficiently loads the Kb molecules in the thymus of these animals. The animals were additionally constructed on a RAG-$2^{-/-}$ background (Shinkai et al., *Cell* 68:855–867 (1992)), thereby guaranteeing exclusive expression of this TCR on the surface of T lineage cells. In these experiments, fetuses were dissected at day 15.5, as it was observed that the development of N15 tg RAG-$2^{-/-}$ animals was slightly slower than that of the corresponding wild type C57BL/6 animals.

After five additional days of FTOC, 60% of N15 TCR tg RAG-$2^{-/-}$ H-$2^b$ thymocytes were DP and 24% were CD8+ SP thymocytes (FIG. 4A). Addition of 10-5 M VSV8 peptide to the N15 FTOCs 18 hours prior to analysis results in massive depletion of CD4+ CD8+DP thymocytes with a reduction from 60% to 21 (FIG. 4B). zVADfmk completely blocks this antigen-induced depletion (FIG. 4C). Importantly, zVADmk, a compound identical to zVADfmk (FIG. 1) except for the absence of the fluoride atom which is required for the irreversible inhibition of caspases, has no effect on the antigen-induced deletion of DP thymocytes (FIG. 4D). Hence, inhibition of enzymatic function is a prerequisite for protecting DP thymocytes from deletion by specific antigen. Exposure of the FTOC to the DMSO solvent prior to VSV8 treatment has no effect (FIG. 4E). The depletion of DP thymocytes is specifically induced by the VSV8 peptide; addition to the FTOC of an equivalent amount of the unrelated SEV9 Sendai virus-derived peptide, which binds to Kb with a comparable affinity to that of VSV8 but which is not recognized by the N15 TCR, does not result in thymocyte death (FIG. 4F).

Histological Analysis of Antigen-Induced Apoptosis in FTOC of N15 TCR tg RAG-$2^{-/-}$ H-$2^b$ Mice: Blockade of Cell Death by zVADfmk Negative selection results in apoptosis of DP thymocytes as judged by morphological criteria or induction of DNA fragmentation as analyzed by gel electrophoresis or TUNEL assay (Murphy et al. (1990); Surh and Sprent, *Nature* 372:100–103 (1994)). Apoptosis in this TCR tg system was confirmed to be induced by the VSV8 peptide in N15 FTOC using a terminal deoxynucleotidyl transferase (TdT) assay on histological sections. This method exploits the fact that apoptosis results in DNA cleavage, the ends of which serve as a substrate for the TdT enzyme, allowing cells undergoing death to be labeled with biotinylated dUTP. Sections were prepared from fetal thymic lobes, cultured as described above, and treated for 4 hours with 10-5M VSV8 peptide with either no pretreatment or a 1-hour pretreatment with zVADfmk or zVADmk. This early time point was chosen for the characterization, as it was previously observed that after overnight exposure to VSV8, dying DP thymocytes from adult animals were already removed by an efficient process involving the non-lymphoid stromal components of the thymus. The effective removal of corpses has been previously described in both tg and non-tg thymuses as well (Surh and Sprent, (1994)).

VSV8 treatment resulted in an obvious increase in the number of TdT positive cells as compared to the control culture which was not exposed to the VSV8 peptide. Pretreatment with zVADfmk prior to VSV8 addition reduces the number of TdT+ cells to that of the control. In contrast, zVADmk pretreated cultures which were exposed to VSV8 had levels of TdT positive cells similar to cultures treated with VSV8 alone. Table 1 shows a quantitative tabulation of the immunohistological results for three N15 tg RAG-2$^{-/-}$ H-2$^b$ FTOCs and a littermate control non-tg RAG-2$^{-/-}$ FTOC. Thus, the depletion of DP thymocytes in the N15 TCR tg RAG-2$^{-/-}$ H-2$^b$ FTOC is blocked specifically with a cysteine protease inhibitor, and this inhibition correlates with a reduction in the number of apoptotic cells as determined by TdT assays. This is the first demonstration that inhibition of a caspase(s) prevents apoptotic cell death induced by antigen triggering of the TCR on immature DP thymocytes.

TABLE 1

Quantitation of cell death in FTOC by TUNEL assay
TdT positive cells
mm2

|  | N15tg #1 | N15tg #2 | N15tg #3 | non-tg |
|---|---|---|---|---|
| Treatment |  |  |  |  |
| Control | 7 | 28 | 7 | 1 |
| VSV8 | 429 | 456 | 441 | 9 |
| zVADfmk + VSV8 | 6 | 1 | 2 | 6 |
| zVADmk + VSV8 | 360 | 525 | 461 | Not Determined |

TCR-Triggered Activation of Caspase(S): A Biochemical Analysis

Although the above results clearly demonstrate that the zVADfmk cysteine protease inhibitor can block antigen-triggered cell death, it remained to be determined whether TCR ligation specifically activates a cysteine protease. Members of the caspase family exist as proenzymes which are cleaved by an activation step to give rise to ~20 KD and ~12 KD subunits (reviewed in Henkart, *Immunity* 4:195–201 (1996)). The heterodimeric subunits then associate to form a tetramer. Because the tetramer but not the inactive proenzyme binds the substrate, a biochemical assay was developed to examine the state of caspases in thymuses of unstimulated or in vivo VSV8-triggered N15 tg mice. To this end, several possible substrates were tested, including biotin-YVADamk and biotin-DEVDamk (FIG. 1). Because the biotin-DEVDamk substrate appears to have the highest affinity for the thymic caspase, only this data is presented.

Figure 2A:
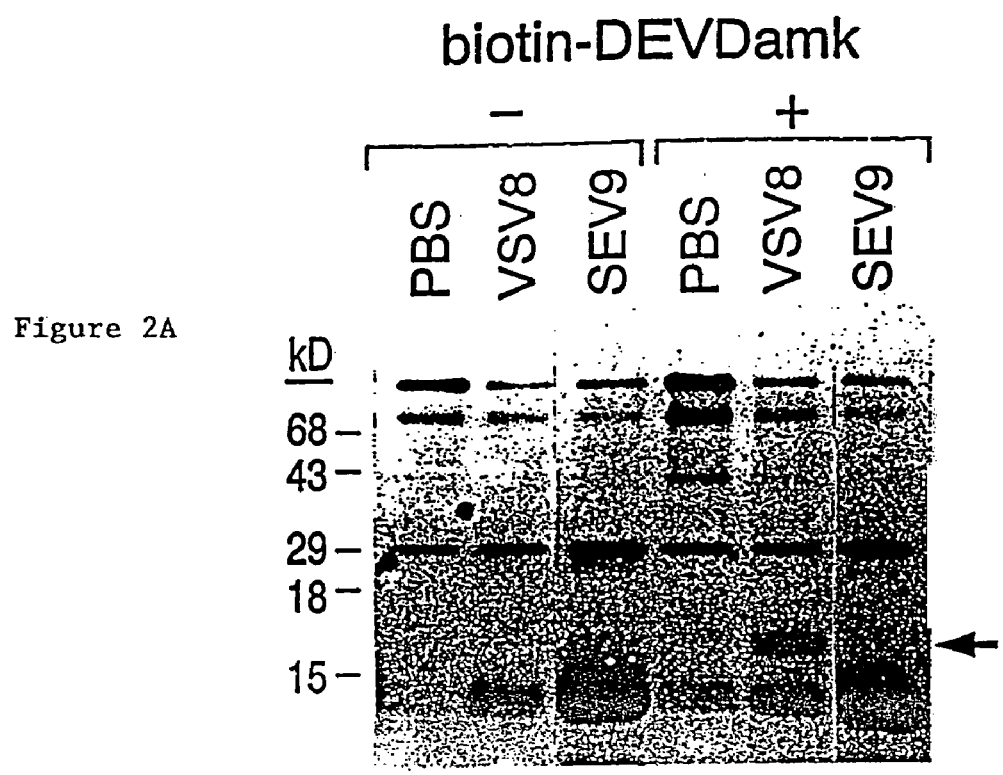
FIGS. 2A–2D show the results of Western blot analysis, which reveal antigen-induced activation of a thymic caspase. Arrows indicate the position of the activated thymic caspase subunit which binds the biotin-DEVDamk.
Figure 2B:
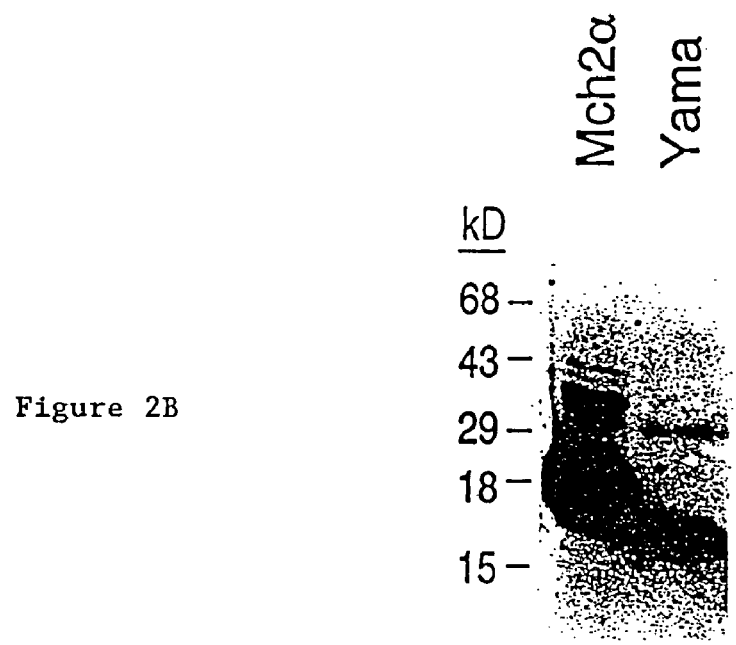

N15 transgenic RAG-2-H-2$^b$ mice were injected in the tail vein with PBS, 24 mg VSV8 or control SEV9 peptide, and extracts were prepared from the thymocytes of these adult mice 2 hours after injection. Lysate equivalent to 2×10$^6$ thymocytes was incubated with or without 2 mM biotin-DEVDamk, which binds irreversibly to caspases with varying rates depending on the specific protease. Subsequently, the treated lysates were analyzed by 12.5% SDS-PAGE and blotted onto nitrocellulose. The membranes were then incubated with streptavidin horseradish peroxidase and developed by ECL. A band of approximately 17 kD is induced in the 2-hour VSV8 treated thymocytes (FIG. 2A). This band is not found in lysates from thymuses of PBS or SEV9 injected animals, and is not detected in thymic lysates without prior incubation with biotin-DEVDamk (FIG. 2A). As expected, purified, recombinant Yama/caspase-3 and Mch2a (caspase-6) proteases bind the biotin-DEVDamk substrate in this assay (FIG. 2B).

The above functional studies, utilizing zVADfmk and the biochemical analysis with biotin-DEVDamk, collectively show that cysteine proteases are activated during antigen-induced negative selection in the thymus. Whether the same caspase(s) interacts with both of these inhibitors remains to be determined. This possibility was tested by competitive inhibition analysis wherein the above thymic lysates were first preincubated with up to 1000-fold molar excess of zVADfmk prior to addition of the biotin-DEVDamk. If both substrate inhibitors bound to the same enzyme, then the non-biotin labeled zVADfmk would block the ability of biotin-DEVDamk to bind to the activated thymic caspase and hence, eliminate detection of the ~17 kD subunit by streptavidin horseradish peroxidase. Alternatively, if these inhibitors bound to different enzymes, then there would be no change in the appearance of the caspase band as detected by biotin-DEVDamk.

Figure 2C:
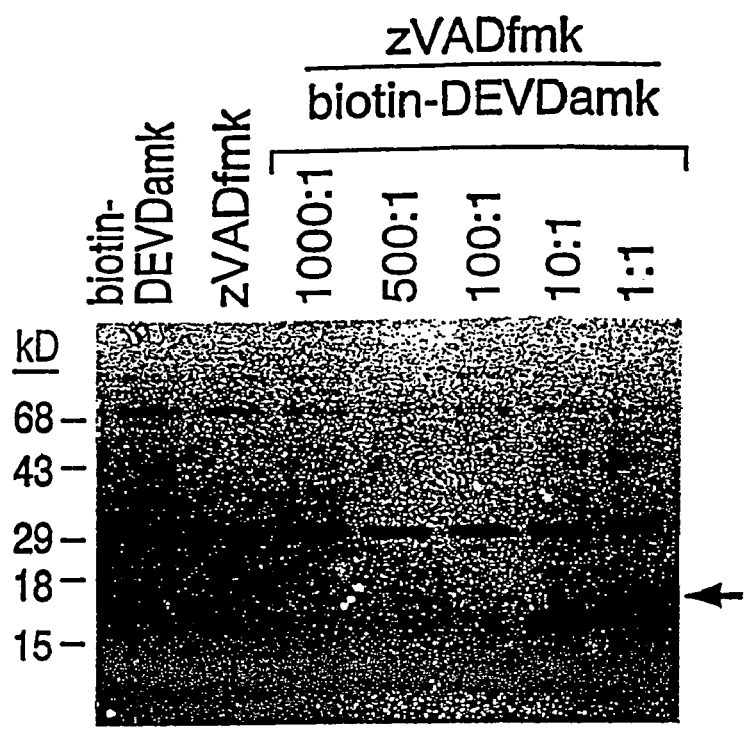
Figure 2D:
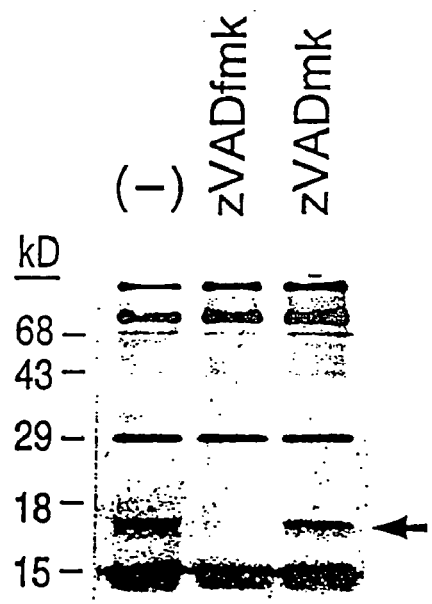

FIG. 2C shows that if the thymic lysates are incubated first with zVADfmk at molar concentrations ranging from 1000- to 100-fold that of the biotin-DEVDamk substrate, the ~17 kD band is no longer detectable by Western blot analysis. In contrast, at lower zVADfmk:biotin-DEVDamk ratios (10:1 or 1:1), the biotin-DEVDamk substrate is bound by the TCR-triggered cysteine protease and therefore detected as a ~17 kD biotinylated inhibitor-enzyme complex. Thus, the irreversible binding of zVADfmk, which blocks VSV8-induced depletion of the DP thymocytes in FTOC, competes with the biotin-DEVDamk substrate for binding to the same ~17 kD band. This result links the antigen-induced negative selection of thymocytes, as measured by depletion of DP thymocytes in FTOC, to the appearance of an activated cysteine protease detectable in the thymuses of mice undergoing negative selection. FIG. 2D shows that while 100-fold molar excess of zVADfmk blocks binding of the biotin-DEVDamk substrate to the antigen-activated cysteine protease, the same excess of zVADmk does not block this interaction. This finding is consistent with the observation that zVADmk fails to block antigen-induced depletion of the DP thymocytes in FTOC.

Localization of Activated Caspase to TCR-Triggered Corticol Thymocytes in N15 tg RAG-2$^{-/-}$ H-2$^b$ Fetal and Adult Mice To localize the activated caspase within the thymus of fetal and adult N15 tg RAG–/– H-2$^b$ mice, two-color immunohistological analysis was performed using biotin-DEVDamk and anti-CD4 mAb. In the N15 RAG$^{-/-}$ H-2$^b$ mice, CD4 staining is essentially limited to the DP thymocytes because the N15 TCR is class I MHC-restricted, resulting in positive selection of CD8+ SP cells exclusively. The majority of thymocytes demonstrate CD4 staining (red/brown), consistent with the large percentage of DP thymocytes present in the thymus of these animals. Staining with biotin-DEVDamk (blue) is negative. In contrast, 4 hours after treatment with VSV8, the CD4 staining became patchy, and the morphology of the CD4 cells was altered, with less discrete cell boundaries. In addition, there is widespread biotin-DEVDamk staining throughout the cortex, indicative of antigen-induced activation of a thymic caspase. Consistent with the biochemical analysis, this activation is blocked by pretreatment with zVADfmk, but not with pretreatment with zVADmk.

The same staining pattern is evident in adult N15 tg RAG-2$^{-/-}$ H-2$^b$ mice. Thymic sections of N15 tg RAG-2$^{-/-}$ H-2$^b$ animals were positive for anti-CD4 reactivity and negative for that of biotin-DEVDamk. However, 4 hours following tail vein injection of VSV8 peptide, the thymic section demonstrated widespread biotin-DEVDamk staining, as well as the same alterations in anti-CD4 reactivity as seen in the VSV8-treated FTOCs. PBS injection does not induce damage to the CD4+ thymocytes or detectable activation of the cysteine protease. Thus, deletion of DP thymocytes occurs through antigen-stimulated activation of a cysteine protease in both FTOC and adult mice, and this activity localizes to the thymocytes themselves.

EQUIVALENTS

Those skilled in the art will recognize, or be able to ascertain, using no more than routine experimentation, many equivalents to the specific embodiments of the invention described herein. Such equivalents are intended to be encompassed by the following claims:

We claim:

1. A method of identifying an agent which enhances the activity of a caspase or procaspase, wherein said caspase or procaspase is expressed in immature thymocytes as a result of T cell receptor stimulation with SEQ ID NO: 9, and wherein said caspase mediates immature thymocyte susceptibility to cell death, comprising the steps of:
   (a) contacting a caspase or procaspase expressed in immature thymocytes as a result of T cell receptor stimulation with SEQ ID NO: 9, with a caspase substrate in the presence of the agent; and
   (b) comparing the activity of said caspase or procaspase in the presence of the agent with the activity of said caspase or procaspase in the absence of the agent, wherein enhancement of the activity of said caspase or procaspase in the presence of the agent is indicative that the agent is one which enhances the activity of said caspase or procaspase.

2. A method of identifying an agent which enhances the activity of a caspase or procaspase, wherein said caspase or procaspase is expressed in immature thymocytes as a result of T cell receptor stimulation with SEQ ID NO: 9, and wherein said caspase is necessary for apoptosis, comprising the steps of:
   (a) contacting the caspase or procaspase expressed in immature thymocytes as a result of T-cell receptor stimulation with SEQ ID NO: 9, with biotin-DEVDamk in the presence of the agent; and
   (b) comparing the activity of said caspase or procaspase in the absence of the agent, with the activity of said caspase or procaspase in the absence of the agent, whereby enhancement of the activity of said caspase or procaspase in the presence of the agent is indicative that the agent is one which enhances the activity of said caspase or procaspase.

3. The method of claim 1, wherein the enhanced procaspase or caspase activity results from prolonging the duration of the activity.

4. The method of claim 1, wherein the enhances activity of caspase or procaspase results from increased conversion of procaspase to caspase.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Gln Ala Cys Xaa Gly
1              5

(2) INFORMATION FOR SEQ ID NO:2:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Tyr Val Ala Asp
1

(2) INFORMATION FOR SEQ ID NO:3:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:3:

Asp Glu Val Asp
1

(2) INFORMATION FOR SEQ ID NO:4:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Phe Ala Pro Gly Asn Tyr Pro Ala Leu
 1               5

(2) INFORMATION FOR SEQ ID NO:5:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (xi) SEQUENCE DESCRIPTION: SEQ ID NO:5:

CTCGAGACCT GTGTGGATTA AAAACCTCTC TGATTCTGGT TTGCTTTTCT GTTTCCAAGC        60

AGGGGTGAGA GGAGACTCCG TGACCCAGAC AGAAGGCCTG                            100

(2) INFORMATION FOR SEQ ID NO:6:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:6:

GCGGCCGCTT GGGCCCAAGA AACTGTCATC AAACGTACGT GCTATAACCT TCAGTCTGGT        60

ACCTGCTCC                                                              69

(2) INFORMATION FOR SEQ ID NO:7:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:7:

ATCGATTCCC CTTCTTGTCT GTATTTACAT CTTTTGTTTT CTTCTCTTCT AGGATCAGCA        60

GATTCTGGGG TTGTCCAGTC TCCAAG                                            86

(2) INFORMATION FOR SEQ ID NO:8:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:8:

GCGGCCGCAC GTGGGGCCCC AGCTCACCTA AAACCGTGAG CCTGGTGCCG GGACCG            56

(2) INFORMATION FOR SEQ ID NO:9:

(i) SEQUENCE CHARACTERISTICS:
        (A) LENGTH: 8 amino acids
        (B) TYPE: amino acid
        (C) STRANDEDNESS: single -continued

```
    (D) TOPOLOGY: linear (ii) MOLECULE TYPE: peptide (xi) SEQUENCE DESCRIPTION: SEQ ID NO:9:

Arg Gly Tyr Val Tyr Gln Gly Leu
1               5
```